(12) United States Patent
Wang et al.

(10) Patent No.: US 8,174,703 B2
(45) Date of Patent: May 8, 2012

(54) METHOD FOR FABRICATING A SENSOR, A SENSOR, AND A METHOD FOR SENSING

(75) Inventors: Wenhui Wang, Lowell, MA (US); Xingwei Wang, Lowell, MA (US)

(73) Assignee: University of Massachusetts, Lowell, MA (US)

( * ) Notice: Subject to any disclaimer, the term of this patent is extended or adjusted under 35 U.S.C. 154(b) by 410 days.

(21) Appl. No.: 12/436,592

(22) Filed: May 6, 2009

(65) Prior Publication Data
US 2009/0279099 A1    Nov. 12, 2009

Related U.S. Application Data

(60) Provisional application No. 61/050,820, filed on May 6, 2008.

(51) Int. Cl.
*G01B 9/02* (2006.01)
(52) U.S. Cl. .......................... 356/480; 385/13
(58) Field of Classification Search .................. 356/480, 356/519; 385/12, 13
See application file for complete search history.

(56) References Cited

U.S. PATENT DOCUMENTS

| | | | |
|---|---|---|---|
| 4,652,744 A | 3/1987 | Bowers et al. | |
| 4,942,767 A | 7/1990 | Haritonidis et al. | |
| 5,087,124 A | 2/1992 | Smith et al. | |
| 5,101,664 A | 4/1992 | Hockaday et al. | |
| 5,247,490 A | 9/1993 | Goepel et al. | |
| 5,301,001 A | 4/1994 | Murphy et al. | |
| 5,381,231 A | 1/1995 | Tu | |
| 5,559,358 A | 9/1996 | Burns et al. | |
| 5,747,705 A | 5/1998 | Herb et al. | |
| 5,891,747 A | 4/1999 | Farah | |
| 6,820,487 B2 | 11/2004 | Esashi et al. | |
| 7,054,011 B2 * | 5/2006 | Zhu et al. ..................... | 356/480 |
| 7,149,374 B2 | 12/2006 | Lagakos et al. | |
| 2004/0047536 A1 | 3/2004 | Pickrell et al. | |
| 2005/0157305 A1 | 7/2005 | Yu et al. | |
| 2007/0006663 A1 | 1/2007 | Zerwekh et al. | |

OTHER PUBLICATIONS

Gander, et al. "Embedded Micromachined Fiber-Optic Fabry-Perot Pressure Sensors in Aerodynamics Applications," IEEE Sensors Journal, vol. 3, No. 1, Feb. 2003, pp. 102-107.
Wang, et al. "An Ultra-Sensitive Optical MEMS Sensor for Partial Discharge Detection," Journal of Micromechanics and Microengineering, 2005, vol. 15, pp. 521-527. Lee, et al. "A Novel Fiber Bragg Grating Acoustic Emission Sensor Head for Mechanical Tests." Scripta Materialia, vol. 53, 2005, pp. 1181-1186.
Xu, et al. "Miniature All-Silica Fiber Optic Pressure and Acoustic Sensors." Optics Letters, vol. 30, No. 24, Dec. 15, 2005, pp. 3269-3271.

* cited by examiner

*Primary Examiner* — Tarifur Chowdhury
*Assistant Examiner* — Jonathan Hansen
(74) *Attorney, Agent, or Firm* — Hamilton, Brook, Smith & Reynolds, P.C.

(57) ABSTRACT

A method for fabricating a sensor, a sensor so fabricated, and a method for sensing a stimulus are provided. The method includes providing an elongated open channel, such as, a V-groove, in a substrate, the open channel providing a first surface; removing at least some material from at least a portion of the open channel to provide a second surface displaced from the first surface; positioning a diaphragm on the second surface; and positioning an elongated wave-guide having a beveled end in the elongated open channel wherein the beveled end is positioned over the diaphragm to define an interferometric cavity between the diaphragm and the outer surface of the wave-guide. The sensor so fabricated can provide an effective sensor for detecting acoustic emission waves, among other pressure waves.

32 Claims, 25 Drawing Sheets

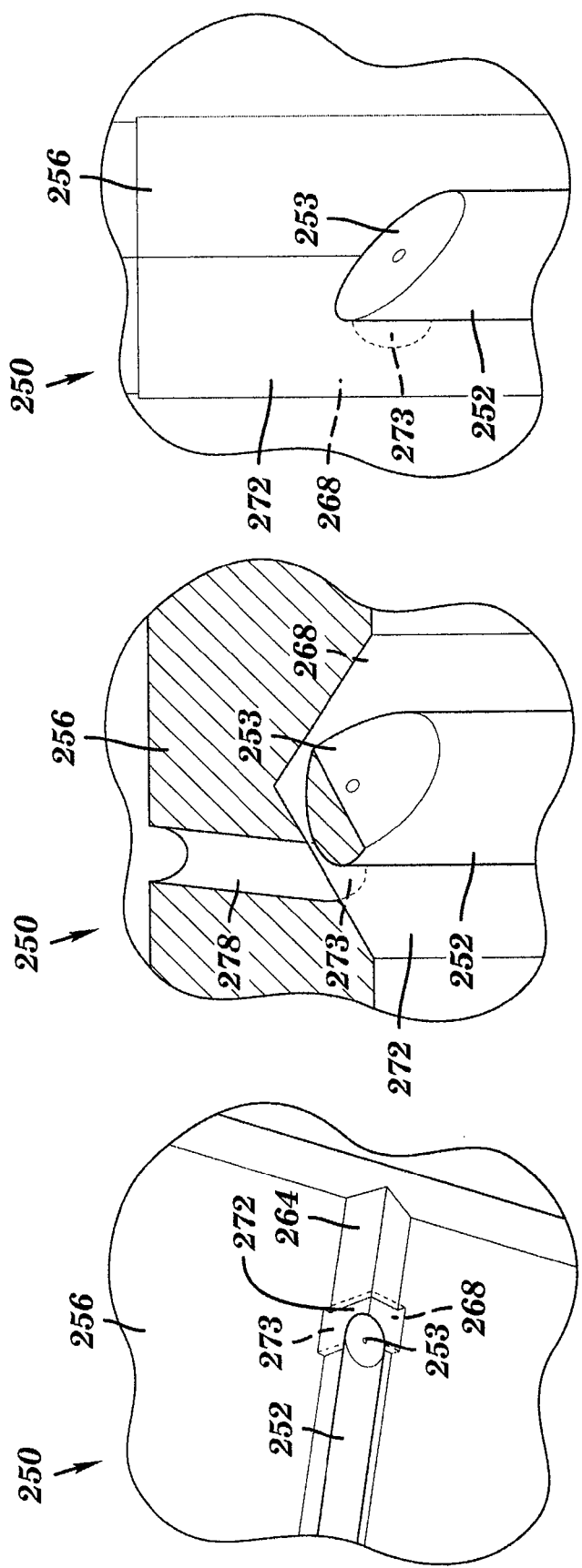

METHOD FOR FABRICATING A SENSOR, A SENSOR, AND A METHOD FOR SENSING

CROSS-REFERENCE TO RELATED APPLICATION

This application claims priority from pending U.S. Provisional Patent Application 61/050,820 filed on May 6, 2008, the disclosure of which is included by reference herein in its entirety.

BACKGROUND

1. Technical Field

The present invention generally relates to sensors and methods for fabricating sensors. More particularly, the present invention relates to sensors, for example, interferometric sensors, fabricated by photolithographic methods having improved reliability and sensitivity.

2. Background of the Invention

Acoustic emission (AE) monitoring has been proven as a suitable nondestructive technology for structure integrity monitoring, diagnostics, and prognostics, among other things. For example, elastic strain waves generated by rapid release of energy produce AE waves during dislocations in materials. These dislocations can be produced, for example, by fatigue cracks (and their growth), impact, inter-surface slippage, twinning, phase transformations, plastic deformation, and corrosion fatigue.

In order to detect AE activity, AE sensors are typically integrated into the target structure to detect and monitor characteristic signals. Typically, the detected (and, typically, recorded) signals are compared to the theoretical and standard sample signal waveforms. The comparison of the waveforms can be used to determine whether the AE activity detected is from material damage or environmental noise. When a sensor array is used, the location of the AE source can be determined. Typical applications of AE detection include their use on pressure vessels, storage tanks, heat exchangers, piping, reactors, aerial lift devices, and nuclear power plants and equipment, among many other types of structures that can be monitored.

Aircraft fatigue monitoring is a prime example of the use of AE monitoring. For example, critical structures within an aircraft, such as, the connecting lugs between the wings and the main fuselage, can be monitored with an AE sensor to detect fatigue cracking. In such applications, an AE sensor should impose the least impact to the structure's weight, surface shape, and mechanical/chemical properties. Therefore, it is preferred that an AE sensor be compact, lightweight, reliable, sensitive, and have low power consumption.

AE sensing can also be used in partial discharge (PD) acoustic detection in high voltage transformers in the power industry. In this application, the principal considerations for selection of AE sensors are immunity to electromagnetic interference and immunity to chemical erosion.

Typical prior art sensors that are used for AE detection include piezoelectric sensors, Fiber-Bragg-Grating (FBG) sensors, and Fabry-Perot (F-P) optical fiber sensors. Of these types of AE sensors, piezoelectric sensors are most widely used because of their high sensitivity, low cost, and ease of use. However, piezoelectric sensors are characterized by the following disadvantages:

1. Most traditional piezoelectric AE sensing systems are bulky. The piezoelectric disk is typically so brittle that special packaging to prevent breakage is typically required. In addition, since electrical signals cannot be transmitted far away without electrical amplifiers, piezoelectric sensors require electrical connections and associated electrical devices, which greatly increase the size and the difficulty of mounting piezoelectric sensors. Furthermore, the complexity of piezoelectric systems typically decreases the reliability of systems employing these sensors.
2. Piezoelectric AE sensors normally have large contact surfaces. Typically, such sensors are 6.35 mm or larger in diameter. As a consequence, the output signal from a piezoelectric AE sensor comprises the integration of all points within the contact area. This inherently decreases the accuracy of the piezoelectric sensor.
3. Piezoelectric AE sensors are electrical devices and, as such, are also sensitive to electromagnetic noise. Therefore, piezoelectric AE sensors require special signal processing methods to minimize their sensitivity to noise. Moreover, piezoelectric AE sensors are not suitable in some environments, such as, to monitor nuclear power equipment.
4. In addition, piezoelectric AE sensors are limited by the electronic device and the Curie temperature of the piezoelectric components. Piezoelectric AE sensors are not suitable for applications where the environment temperature is over 573 K.

Optical AE sensors have shown high resolution and accuracy using an interferometric detection technique, such as, in Fabry-Perot (F-P) cavity or Fiber-Bragg-Grating (FBG) AE sensors. The small size and geometrical flexibility of such optical AE sensors make them easy to be mounted in positions close to critical locations, for example, where cracking and damage are expected to initiate, while optical AE sensors typically do not influence the mechanical properties and performance of target structure. Optical connections and non-conducting sensors make the system immune to electromagnetic interference, insensitive to thermal variation, and inert to chemical erosion. Optical AE sensors can transmit a signal faster and farther than electrical devices. Another outstanding advantage of optical AE sensors is their capability of survival in high-pressure and high-temperature cure environments that are common during structure fabrication, system integration, and daily use.

However, FBG-type AE sensors and high finesse F-P-type AE sensors are typically sensitive to the noise from the environment. The spectrum of these optical sensors is so sharp that small deviations of the laser wavelength or small changes in the environment can shift the spectrum greatly. FBG sensors and intrinsic F-P interferometric (IFPI) sensors may drift greatly due to the uncertain polarization state, refractive index variation with temperature, and unreliable bonding points. Currently, the most common prior art solution is to lock the laser wavelength to the center of the optimized modulation position in the reflection spectrum. However, locking the laser wavelength increases the complexity and cost of the optical AE sensor system. This problem becomes intolerable when multiple sensors are used to establish a network, and each of optical AE sensors needs an independent monitoring and tuning system. Another solution is to use a short FBG or a short-cavity-length F-B sensor. Also, the sensing area of an optical AE sensor, such as, the length of the FBG, should be less than the wavelength of the acoustic wave detected. Otherwise, the output from the FBG-type AE sensor will be distorted by the averaging effect on the change of the grating pitch or FBG cavity. However, this typically will decrease the sensitivity of the FBG AE sensor and increase the fabrication difficulty of F-P AE sensor.

Diaphragm-based, extrinsic F-P interferometric (EFPI) optical sensors can avoid the disadvantages mentioned above optical AE sensors. EFPI AE sensors are small and compact in size while maintaining the advantages of the optical fiber sensors at the same time. According to aspects of the present invention, as will be discussed below, a diaphragm of an F-P sensor can be fabricated by MEMS technology, which has high potential for providing low cost, good repeatability, and high yield.

As is known in the art, because acoustic waves from AE are typically from 100 k Hz to 1 MHz, a spectrum demodulation method is typically not fast enough for EFPI AE sensors and an intensity demodulation method is normally used. However, as will be discussed below, aspects of the present invention overcome or minimize this disadvantage of EFPI AE sensors.

Moreover, accurate cavity length control is very important for EFPI AE sensor fabrication and high quality thin diaphragm fabrication for EFPI AE sensors are difficult to achieve with current design and fabrication techniques. For example, although cavity length control of 3 nanometers (nm) precision has been reported, the diaphragm thickness used was about 5 μm is too thick to achieve the high sensitivity desired for AE detection. This undesirable diaphragm thickness limitation and poor repeatability was a result of the fabrication method used.

Though photolithographic methods have been used in the prior art to fabricate diaphragms, the uniformity of the cavity length in the F-P cavity is difficult to control and the yields are poor.

In addition, prior art methods of mounting optical fibers, whose end face serves as one of the reflection surfaces of F-P cavity, are typically bonded by epoxy glues. The use of such glues introduces problems for F-P-type AE sensors, such as, reduced reliability and spectrum shift caused by temperature variation.

U.S. Pat. No. 5,381,231 of Tu; U.S. Pat. No. 5,087,124 of Smith, et al.; and U.S. Patent Publication 2007/000663 of Zerwekh, et al. all disclose interferometric sensors having optical fibers. However, none of these references provide the teachings or advantages of aspects of the present invention.

The prior art methods of fabricating optical AE sensors cannot meet the requirements of high performance, high yield, and low cost at the same time because of the difficulty in controlling cavity length and diaphragm thickness. Prior art methods of fabrication are complex and costly fabrication process. Accordingly, there is a need in the art for method of fabricating an optical AE sensor that provides precise cavity length control, high sensitivity, good thermal stability and repeatability, simple fabrication and packaging process, and high-volume production. Moreover, there is a need in the art for accurate optical AE sensors having high sensitivity, good thermal stability, and good repeatability. Aspects of the present invention address these shortcomings and disadvantages of the prior art.

SUMMARY OF THE INVENTION

Aspects of the present invention overcome the disadvantages of the prior art by providing sensors, methods of fabricating sensors, and methods of sensing that employ precise dimensional control of critical sensing parameters and enhanced sensitivity that is not found in the prior art. For example, aspects of the invention provide improved interferometric cavity length tolerance, thus increasing fabrication accuracy and repeatability. Aspects may also allow minimization of diaphragm thickness, thus increasing sensor sensitivity.

Aspects of the present invention are based upon the external Fabry-Perot interferometer (EFPI) principle, that is, the illumination of a target diaphragm with a source of electromagnetic radiation, typically, a laser, and the detection of the variation of the interference patterns from the radiation reflected from the diaphragm due to deflection of the diaphragm. Aspects of the present invent may employ standard etching and photolithography processes that are capable of providing high yield at low cost.

Although conventional etching processes are insufficient to provide the rigorous uniformity in cavity length desired, standard, well-controlling etching methods can provide high volume production. Photolithography and other MEMS-related processes are the most important processes commonly used in semiconductor fabrication. Such processes can be used to fabricate ultra precise patterns with ultra-high repeatability and at low cost. In conventional photolithographic methods, patterns are used as masks for other fabrication processes, such as, etching. In aspects of the present invention, cavity length of an EFPI-type AE sensor is established and controlled by photolithography, for example, by photolithography alone.

One aspect of the invention is a method for fabricating a sensor, the method comprising or including providing an elongated open channel in a top surface of a substrate, the open channel providing a first surface and a direction of elongation; removing at least some material from at least a portion of the first surface of the open channel to provide a second surface in the open channel displaced from the first surface; positioning a diaphragm on the second surface, the diaphragm having a top surface and a bottom surface; removing at least some material from the substrate beneath the diaphragm; and positioning an elongated wave-guide having a beveled end in the elongated open channel wherein an outer surface of the wave-guide contacts the first surface and wherein the beveled end is positioned over the diaphragm to define an interferometric cavity between the diaphragm and the outer surface of the wave-guide. For example, the interferometric cavity length may be defined as the length from the top surface of the diaphragm, or the bottom surface of the diaphragm, or both the top and bottom surfaces of the diaphragm to the outer surface of the wave-guide. In one aspect of the invention, multiple diaphragm sensors may be fabricated, for example, on a single substrate. The multiple sensors may be tested after fabrication and, depending upon performance, characterized or selected for use, for example, selected for packaging or storage.

In another aspect of the invention the top surface of the diaphragm or the bottom surface of the diaphragm and/or the wave-guide may be isolated from the surrounding media or mediums. For example, the top surface and the wave-guide may be isolated by some form of sealed enclosure, for example, an enclosure or coating containing or encapsulating a medium having a desired or known refractive index, such as, a gas, for example, air, or a liquid, for example, an oil, or anther compressible material. In another aspect, the bottom surface of the diaphragm may also be isolated, for example, by means of sealing the aperture to provide an aperture having a medium having a desired or known refractive index, such as, a gas, for example, air, or a liquid, for example, an oil, or another compressible material. The bottom surface of the diaphragm may also be exposed to a depression or blind aperture or hole containing the desired medium, such as, air.

In one aspect, the isolated or sealed surface of the diaphragm, for example, the aperture side, may contain the reference medium, such as, air, and the non-isolated or unsealed side of the diaphragm may be exposed to the stimulus.

Though in one aspect of the invention, the bottom surface of the diaphragm may be exposed to the stimulus, in another aspect of the invention, the top surface or the top and bottom surfaces of the diaphragm may be exposed to the stimulus that deflects the diaphragm. For example, in one aspect, the aperture may not pass completely through the substrate, but may be of sufficient depth to permit the diaphragm to deflect under the influence of the stimulus to which the top surface of the diaphragm is exposed. For example, in one aspect, the aperture may be a blind hole having a depth of at least the thickness of the diaphragm, for instance the blind hole may have a depth of from about 0.05 micrometers to about 10 micrometers. In another aspect, the aperture may comprise a through hole completely through the substrate, again, this through hole may be sealed with a sealing agent or compound.

According to aspects of the invention, the stimulus may be one or more of elastic strain waves, compression waves, longitudinal waves, dynamic pressure waves, static pressure, acoustic emission waves, temperature, and acceleration, among other stimuli. In one aspect, providing an elongated open channel in the surface of the substrate may comprise providing an elongated v-groove in the surface of the substrate, for example, etching the top surface of the substrate.

In one aspect, positioning the diaphragm on the second surface comprises depositing a material on the second surface, for example, by growing or depositing one or more layers of polymeric material, for example, a multilayer diaphragm. The diaphragm may comprise a thin film, for example, a thin diaphragm having a thickness less than or equal to about 10 micrometers, or less than or equal to about 1.0 micrometer, for example, between about 0.2 micrometers and about 1.0 micrometers. However, in some aspects of the invention, the diaphragm thickness may be less than about 0.2 micrometers, for example, between about 0.05 to about 0.2 micrometers, though in some aspects, the diaphragm may have a thickness less than about 0.05 micrometers (that is, less than or equal to 50 nanometers).

It is envisioned that the method and devices of the invention may employ semiconductor manufacturing methods and/or micro-electromechanical systems (MEMS) manufacturing methods, for example, photolithography, masking, anisotropic etching, and removal of silicon and germanium and related semiconductor materials, and the like. Semiconductor manufacturing methods and/or MEMS manufacturing methods can provide relative dimensional precision and high dimensional tolerance, for example, of groove or channel depth, width, and/or position, which are uniquely suited for aspects of the invention. In one aspect, the methods of the invention provide more uniform diaphragms, for example, having more consistent thicknesses and properties, compared to the prior art.

The channel may have any conventional cross-section, for example, v-shaped, u-shaped, square, rectangular, or semicircular, among other cross-sectional shapes. In one aspect, the channel comprises a cross section having at least one sidewall, for example, one vertical or inclined wall onto which the diaphragm can be formed and through which an aperture can be provided. In one aspect, the channel may have V-shaped cross-section with a substantially horizontal base, for example, at the bottom of the channel.

According to aspects of the invention, a method is provided in which the length of the interferometric cavity, for example, the length of an F-P cavity, can be held to a tolerance of +/−0.5 micrometers (μm) or finer; for example, held to a tolerance of +/−0.1 μm or finer; or even to a tolerance of +/−0.05 μm or finer. That is, a more repeatable and reliable sensor can be provided than can be provided by the prior art. In particular, in one aspect, the diaphragm may have a thickness of less than 0.05 micrometers or less, and the tolerance of the interferometric cavity length may be held to +/−0.05 micrometers or less.

According to aspects of the invention, one or more components of the sensor may be fabricated individually or substantially simultaneously. For example, one or more channels may be provided in one or more substrates, for instance, channels of varying, length, width, or depth. In addition, one or more recesses, one or more apertures, or one or more diaphragms may be formed or fabricated on one or more substrates. For example, two or more diaphragms of varying thickness and/or varying diameter for different sensor applications may be deposited in one or more channels. In one aspect, one or more apertures, for example, apertures of the same or varying depth and/or the same or varying diameter, or one or more diaphragms may be provided at substantially the same time, for example, by selective etching or selective deposition. For example, two or more sensors may be provided having different requirements but fabricated in substantially the same way, for instance, by the same anisotropic etching process. In one aspect, an array of sensors may be fabricated, for example, on a single substrate, to provide multiple sensors for monitoring and detecting an acoustic occurrence. According to these aspects of the invention, sensor inventories can be reduced and sensor handling and delivery, among other things, can be facilitated.

Another aspect of the invention is a sensor comprising or including: an elongated open channel in a top surface of a substrate, the open channel providing a first surface; a recess in at least a portion of the first surface of the open channel providing a second surface displaced from the first surface; a diaphragm positioned on the second surface, the diaphragm having a top surface and a bottom surface; a cavity in the second surface beneath the diaphragm exposing at least a portion of the bottom surface of the diaphragm; and an elongated wave-guide adapted to transmit electromagnetic radiation, the wave-guide having a beveled end positioned in the elongated open channel wherein an outer surface of the wave-guide contacts the first surface and wherein the beveled end is positioned over the diaphragm to transmit radiation to and receive radiation from the diaphragm and to define an interferometric cavity length between the diaphragm and an outer surface of the wave-guide. For example, the interferometric cavity length may be defined as the length from the top surface of the diaphragm, or the bottom surface of the diaphragm, and/or both the top and bottom surface of the diaphragm to the outer surface of the wave-guide, as discussed above with respect to the media the sensor is exposed to. In another aspect, the second surface displaced from the first surface may be located at a depth in the substrate deeper than the first surface, or be defined by a width wider than the width of the channel. In one aspect, the sensor may comprise one or more interferometric cavities, for example, the multi-cavity configuration discussed above having reflections from two or more surfaces, for instance, from three surfaces. Again, according to aspects of the invention, the stimulus may be one or more of elastic strain waves, compression waves, longitudinal waves, dynamic pressure waves, static pressure, acoustic emission waves, temperature, and acceleration, among other stimuli.

In one aspect, the cavity in the second surface may comprise a blind hole or a through hole or aperture in the substrate.

The through hole or aperture may be positioned to expose at least some of the bottom surface of the diaphragm to the stimulus to be sensed by the sensor. The hole or cavity may have proximal end adjacent the diaphragm and a distal end, or example, an open or closed distal end. When the distal end of the hole or cavity is closed, the distal end may be closed with a rigid or deflectable diaphragm or membrane. For example, in one aspect, the deflectable membrane may be adapted to deflect under the influence of a stimulus and transmit the stimulus through a medium, such as, a gas or liquid, or another compressible material, in the closed cavity to the diaphragm at the proximal end of the hole or cavity. The closed cavity may comprise a sub-atmospheric (that is, a vacuum), an atmospheric, or a super-atmospheric pressure gas or liquid. In another aspect, the elongated waveguide may comprise an optical fiber having a beveled end. The electromagnetic radiation may be any available radiation, including infrared light, ultraviolet light, white light, and visible light, for example, provided by a laser or a diode.

Again, in one aspect, the sensor may provide an interferometric cavity length having a tolerance of +/−0.05 micrometers, or less. The diaphragm thickness may range from about 10 micrometers to about 0.05 micrometers, or less. In one aspect, a sensor is provided that is more reliable, more repeatable, and more sensitive sensor than the prior art.

In one aspect of the invention, the stimulus may be periodic or wave-like whereby the diaphragm may be pushed and pulled repeatedly or periodically. For example, the diaphragm may be pushed and pulled under a varying pressure or varying acoustic wave. In another aspect, the stimulus may be substantially constant, for example, a static pressure wave or a temperature. The pressure may also be superatmospheric or subatmospheric, for example, the stimulus may be a vacuum.

A further aspect of the invention is method for sensing a stimulus comprising or including: providing an elongated open channel in a top surface of a substrate, the open channel providing a first surface; providing a recess in at least a portion of the first surface to provide a second surface displaced from the first depth; positioning a diaphragm on the second surface of the recess, the diaphragm adapted to deflect in response to the stimulus; providing a cavity in the substrate beneath the diaphragm; positioning an elongated wave-guide having a beveled end in the elongated open channel wherein an outer surface of the wave-guide contacts the first surface and wherein the beveled end is positioned over the diaphragm to define an interferometric cavity length between the diaphragm and an outer surface of the wave-guide; transmitting a first electromagnetic signal from the beveled end upon the diaphragm; receiving a second electromagnetic signal reflected from the diaphragm; and comparing the second electromagnetic signal to a reference signal to detect deflection of at least a portion of the diaphragm to characterize the stimulus deflecting the diaphragm. The interferometric cavity length may be defined as the length from the top surface of the diaphragm, and/or the bottom surface of the diaphragm, and/or both the top and bottom surface of the diaphragm to the outer surface of the wave-guide, where the first and second electromagnetic signals may be received and reflected from the top surface of the diaphragm, and/or the bottom surface of the diaphragm, and/or both the top surface and the bottom surface. In addition the cavity in the substrate may be a through hole or an aperture having a distal end positioned to receive a stimulus and transmit the stimulus through the through hole or aperture to the diaphragm. The stimulus may impinge the top surface of the diaphragm, the bottom surface, or both the top and bottom surfaces.

Again, according to aspects of the invention, the stimulus may be one or more of elastic strain waves, compression waves, longitudinal waves, dynamic pressure waves, static pressure, acoustic emission waves, temperature, and acceleration, among other stimuli. In one aspect, positioning a diaphragm on the second surface of the recess may comprise depositing or growing a material on the second surface to form the diaphragm, for example, one or more layers of material. For example, the diaphragm may be grown by thermal oxidation of silicon. The aperture may have an open distal end positioned to receive a stimulus and transmit the stimulus through the aperture In another aspect, transmitting a first electromagnetic signal from the beveled end may comprise transmitting the first electromagnetic signal along the wave-guide whereby the first electromagnet signal is emitted from the beveled end. In another aspect, receiving a second electromagnetic signal may comprise receiving the second electromagnetic signal by the beveled end and transmitting the second electromagnetic signal along the wave-guide. In one aspect of the invention, comparing the first electromagnetic signal to the reference electromagnetic signal to characterize deflection of at least the portion of the diaphragm may comprise transmitting the second electromagnetic signal to an interferometer signal analyzer or a photo detector. In another aspect of the invention, an intensity measurement may be made for a rapid signal response using only one wavelength and photo detector.

In another aspect of the invention, as shown below, the method may further comprise transmitting a source electromagnetic signal along the elongated wave-guide and reflecting the source electromagnetic signal from the beveled end toward the diaphragm; reflecting at least some of the source electromagnetic signal from a sidewall of the waveguide to provide the reference electromagnetic signal; and transmitting at least some of the source electromagnetic signal through the sidewall to provide the first electromagnetic signal.

According to some aspects of the invention, the second signal, for example, a light beam, reflected from the diaphragm will interfere, for example, optically interfere, with the reference beam reflected from the wave-guide sidewall. Any stimulus, for example, an acoustic wave, impacting and deflecting the diaphragm will vary the interference of the second signal with the reference signal whereby the stimulus can be detected and characterized, for example, measured. Two reflected beams—a reference signal reflected from the sidewall and a second signal reflected from the diaphragm— may be forwarded by the wave-guide to an interferometric detector to characterize the diaphragm deflection.

In another aspect, the distal end of the aperture may be an open distal end or a closed distal end. When the distal end of the aperture is closed, the aperture may comprise a sealed cavity, for example, at sub-atmospheric (that is, a vacuum), atmospheric, or super-atmospheric pressure, adapted to transmit the stimulus impacting the closed distal end to the diaphragm.

Again, in the method of the invention, the diaphragm may have a thickness less than 0.05 micrometers, or less, and the interferometric cavity length may have a tolerance of +/−0.05 micrometers, or less.

These and other aspects, features, and advantages of this invention will become apparent from the following detailed description of the various aspects of the invention taken in conjunction with the accompanying drawings.

BRIEF DESCRIPTION OF THE FIGURES

The subject matter, which is regarded as the invention, is particularly pointed out and distinctly claimed in the claims at the conclusion of the specification. The foregoing and other objects, features, and advantages of the invention will be readily understood from the following detailed description of aspects of the invention taken in conjunction with the accompanying drawings, in which:

FIG. 21 is a perspective view, similar to FIG. 18, of another aspect of the invention.

FIG. 22 is a perspective view, partially in cross section, of the aspect of the invention shown in FIG. 21.

FIG. 23 is a plan view of the aspect of the invention shown in FIG. 21.

DETAILED DESCRIPTION

The following detailed description of the figures summarized above will be helpful in understanding the subject matter that is particularly pointed out and distinctly recited in the claims that appear at the conclusion of the specification.

Figure 1:
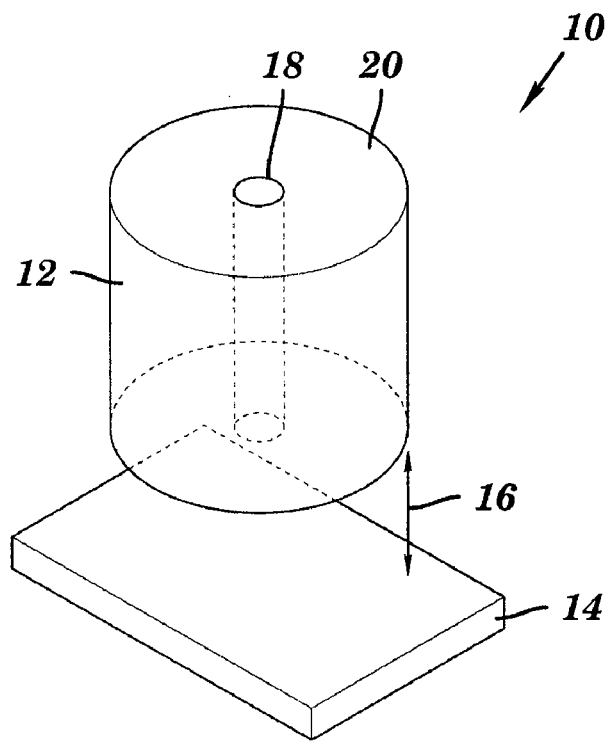
FIG. 1 is schematic diagram of a typical Fabry-Perot (F-P) cavity according to the prior art that can be used for interferometric detection.

FIG. 1 is schematic diagram of a typical Fabry-Perot (F-P) cavity 10 according to the prior art that can be used for interferometric detection. F-P cavity 10 typically includes a wave-guide 12, for example, an optical fiber, positioned adjacent a thin film 14, for example, a diaphragm, to definite a cavity length 16 between the end of wave-guide 12 and thin film 14. As is known in the art, in typical operation, deflection of thin film 14, for example, by an acoustic emission or pressure wave, is detected from variation in the interference between the signal emitted by the wave-guide 12 and signal reflected from thin film 14 back into wave-guide 12. As discussed above, sensors based upon an F-P cavity are sensitive to environmental noise and the geometry of the cavity, for example, as illustrated in FIG. 2.

Figure 2:
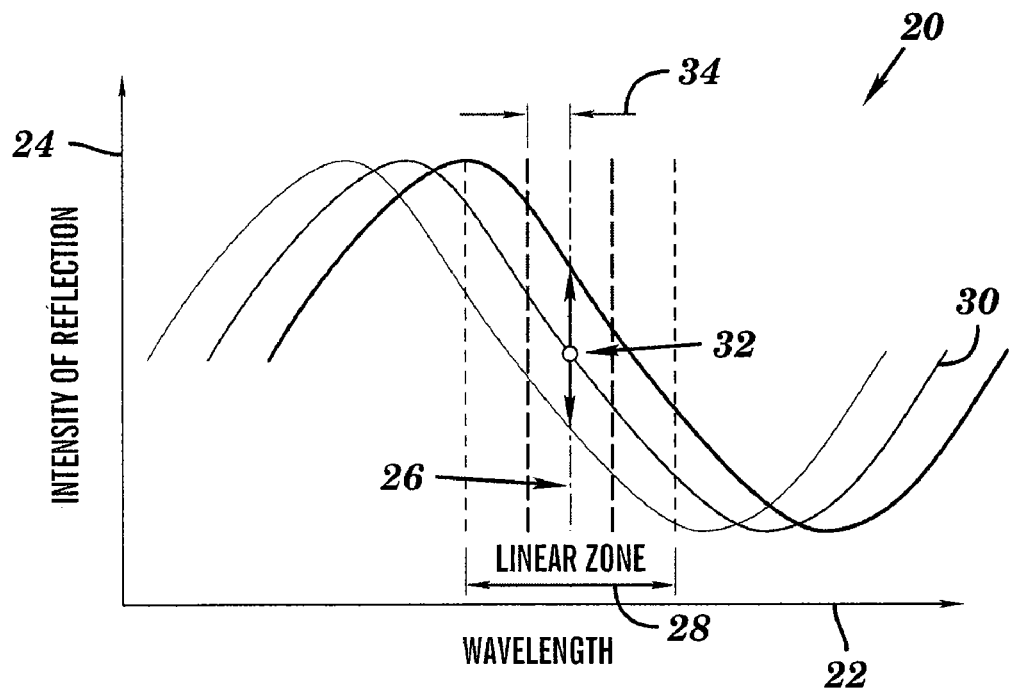
FIG. 2 is graphical representation of the modulation of reflection intensity due to variation in F-P cavity length for the F-P cavity shown in FIG. 1.

FIG. 2 is graphical representation 20 of the modulation of reflection intensity due to variation in Fabry-Perot (F-P) cavity length, for example, variation in cavity length 16 of F-P cavity 10 shown in FIG. 1. The graphical representation 20 includes an abscissa 22 of source wavelength, for example, laser wavelength, and an ordinate 24 of reflection intensity of the source reflected, for example, from thin film 14. As shown in FIG. 2, when thin film 14 (FIG. 1) deflects, the reflection spectrum of the F-P cavity will shift correspondingly. If the laser wavelength is fixed, the reflected laser intensity will be modulated by the movement of thin film 14. To avoid ambiguity and achieve high sensitivity and large dynamic range, according to aspects of the invention, the sensing wavelength may be tuned to the center of linear working zone as shown in FIG. 2. For a fixed source wavelength 26, the linear zone 28 of intensity curve 30 defines an acceptable variation in intensity 32. As also shown in FIG. 2, there is an acceptable deviation or departure 34 due to variation in cavity length 16 from the center of the linear zone 28 and the wavelength of the light source 26. For example, according to an aspect of the present invention, the cavity length 16 can be accurate and not vary by more than +/−0.05 micrometers (μm) under a wavelength of 1.55 μm. For example, in one aspect of the invention, the cavity length analogous to cavity length 16 may range from bout 0.01 μm to about 500 μm, but typically ranges from about 0.5 μm to about 150 μm, and may have a tolerance of +/−0.05 μm, or less.

The intensity curves 29 shown in FIG. 2, that is, the F-P cavity interference fringe, can be described by the expression shown in Equation 1. In Equation 1, $$\phi \propto \cos\left(\frac{4*\pi*n*L}{\lambda}\right) \qquad \text{Equation 1}$$

ø is the intensity of the reflected light, λ is the wavelength, n is the index of the media in the F-P cavity, and L is the cavity length. For example, when a source laser's wavelength is 1.55 μm and the medium in the cavity is air, having a refractive index n=1, Equation 1 indicates that a cavity length change of 0.775 μm will introduce one period spectrum shift (one peak and one valley) at the wavelength position of 1.55 um. If a 1/16 period in the spectrum is chosen as a criterion for an acceptable departure between the center of linear zone 28 and the laser wavelength 26, as shown in FIG. 2, the accuracy of cavity length L should be at least +/−0.05 μm for a laser wavelength of 1.55 μm.

Figure 3A:
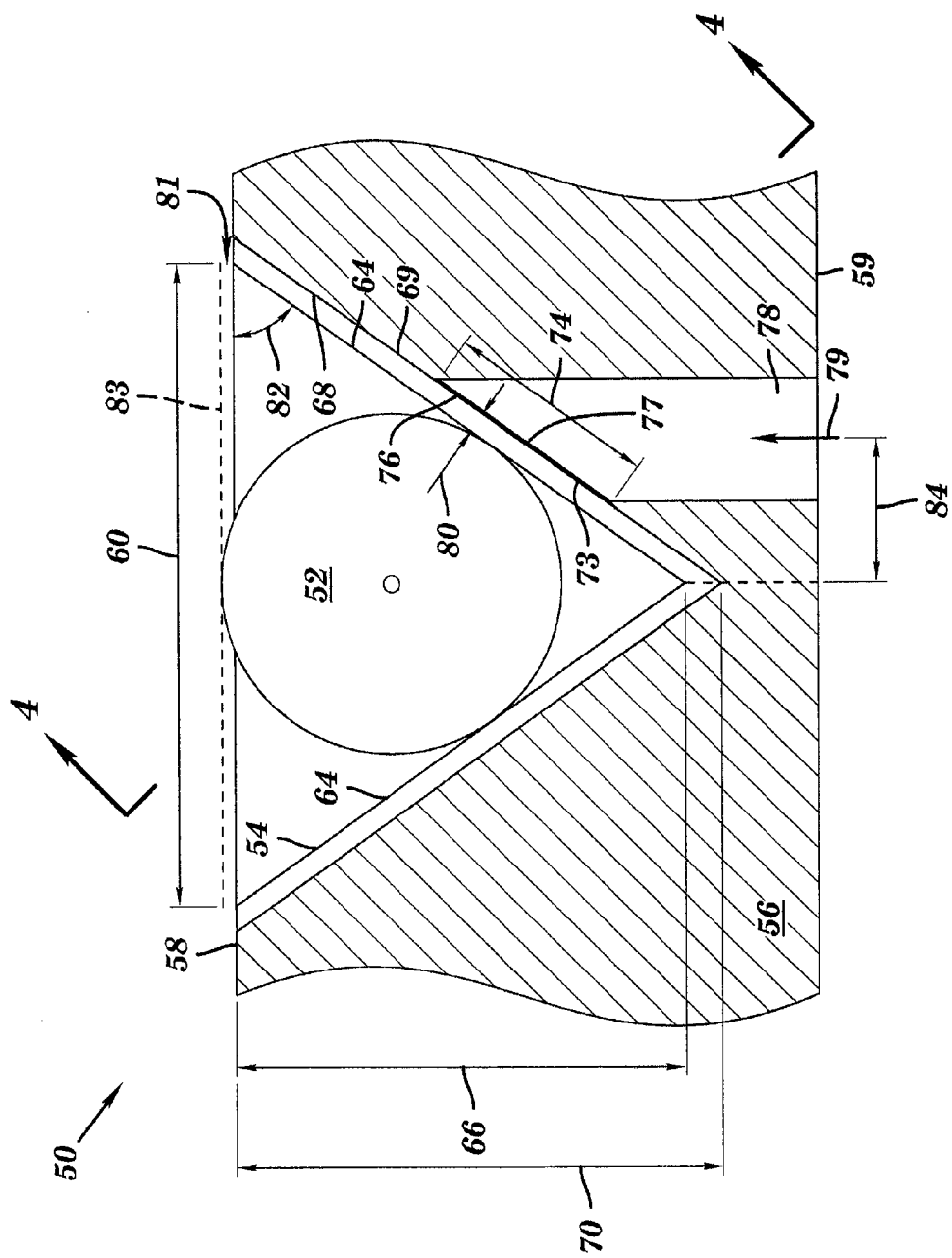
FIGS. 3A, 3B, and 3C are axial views of sensors according to aspects of the present invention.
Figure 3B:
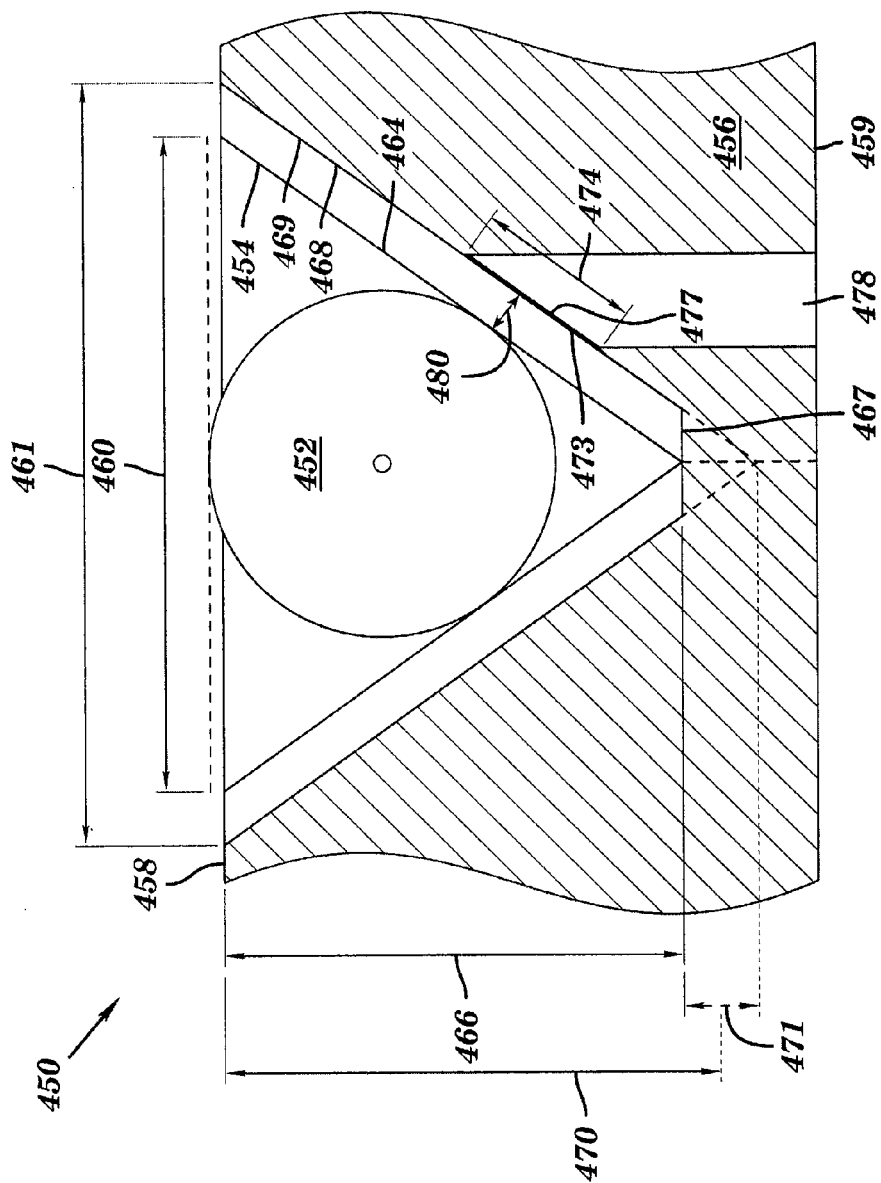
Figure 3C:
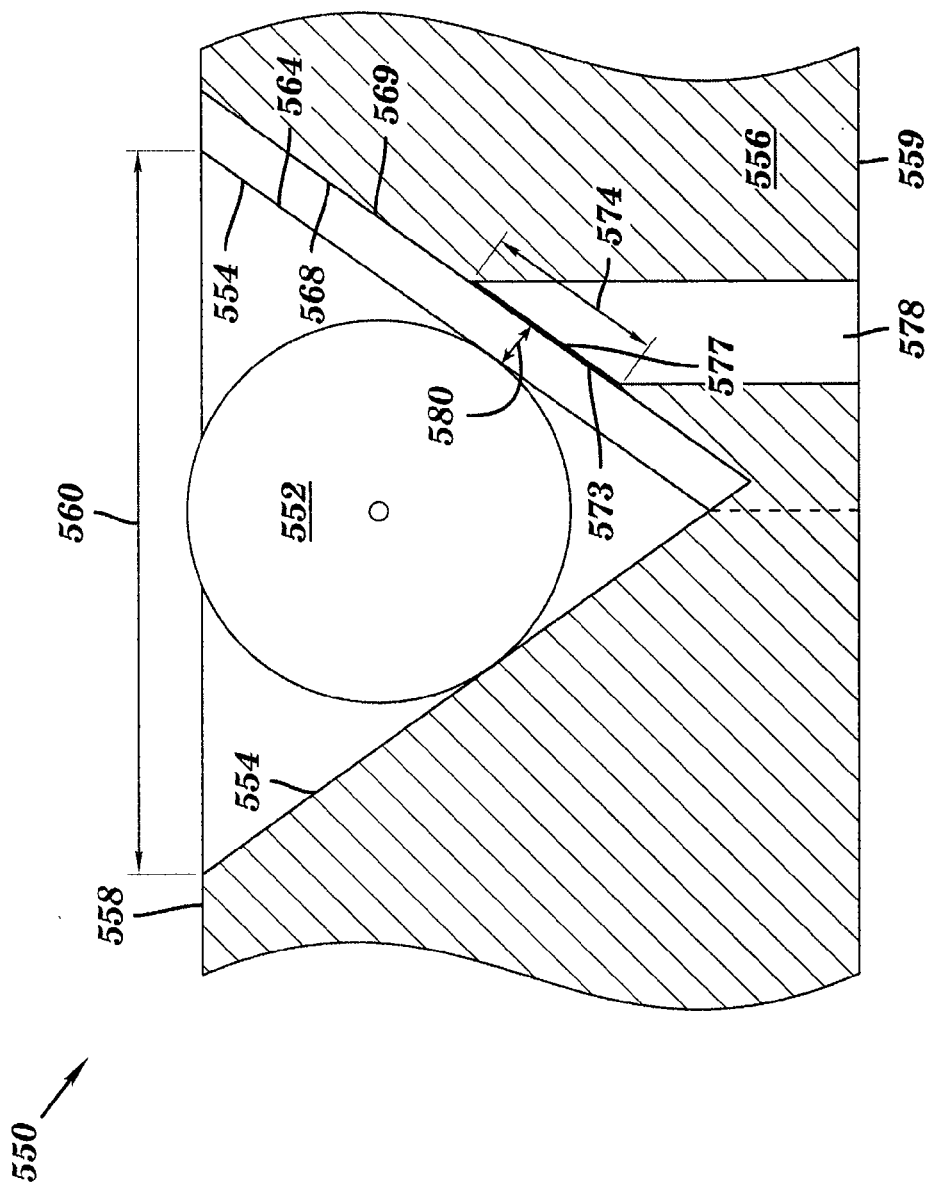
Figure 4:
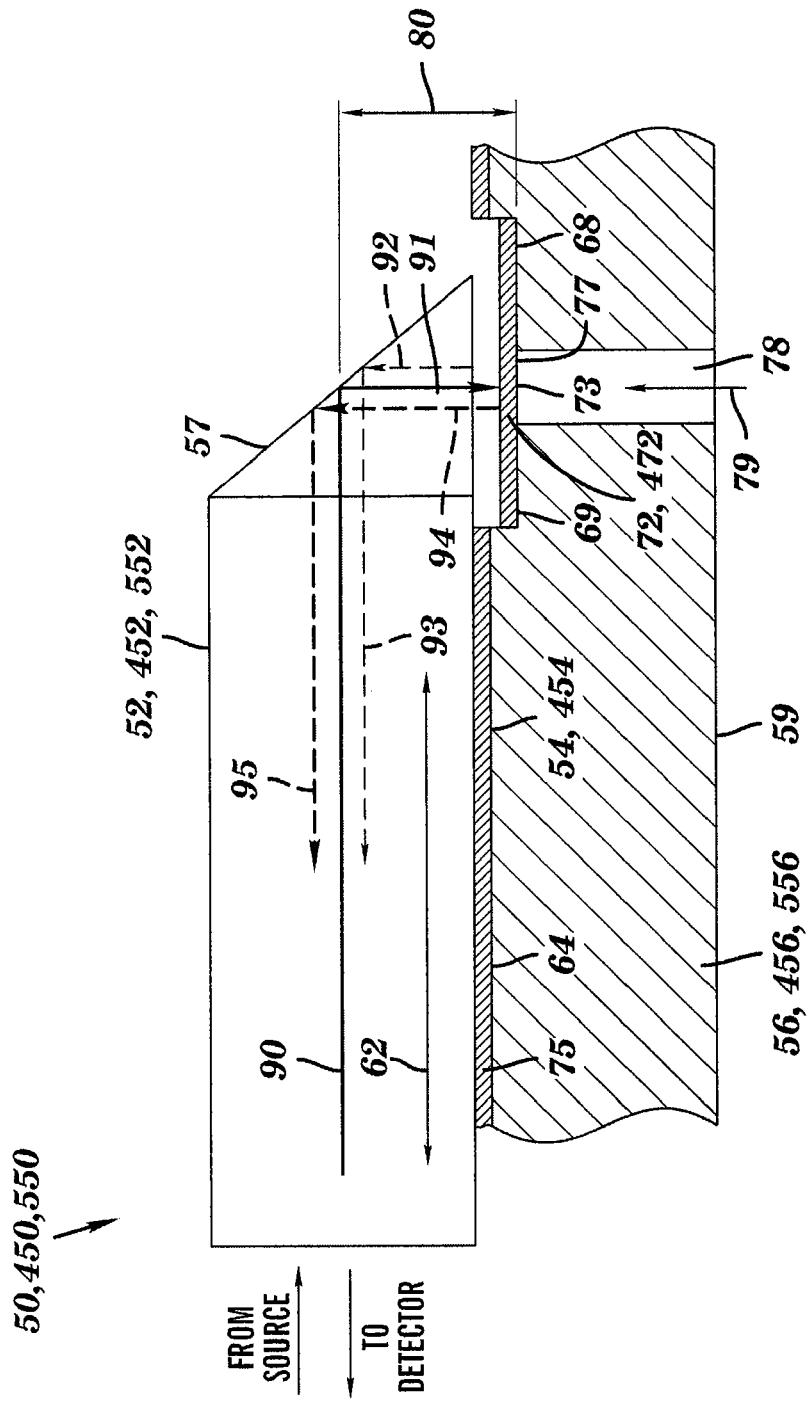
FIG. 4 is a transverse elevation view, partially in cross section, of the sensors shown in FIGS. 3A, 3B, and 3C as viewed allow section lines 4-4 in FIG. 3A.

FIGS. 3A, 3B, and 3C are axial views of sensors 50, 450, and 550, respectively, according to aspects of the present invention that overcomes the disadvantages of the prior art and provides a sensing device that is more accurate, repeatable, and easier to manufacture compared to prior devices. FIG. 4 is a transverse elevation view, partially in cross section, of the sensor 50, 450, and 550 shown in FIGS. 3A, 3B, and 3C, respectively, as viewed allow section lines 4-4 in FIG. 3A.

As shown in FIGS. 3A and 4, sensor 50 includes a wave-guide 52, for example, a fiber optic, positioned in an elongated channel, groove, or recess 54 in a substrate 56, for example, a channel 54 in a top surface 58 of substrate 56. As shown most clearly in FIG. 4, wave-guide 52 may typically comprise a beveled end 57, for example, a polished end beveled at anywhere from about 40 to about 50 degrees, but typically beveled at an angle of between about 43 degrees and about 47 degrees, for example, about 45 degrees. As shown in FIG. 3A, channel 54 has a width 60 at surface 58 and includes a direction of elongation 62, as shown in FIG. 4. Channel 54 provides a first surface 64, for example, at a first depth 66 from surface 58.

According to aspects of the invention, at least a portion of the first surface 64 of channel 54 may be provided with a recess 68 having a second surface 69 displaced from first surface 64. For example, in one aspect, second surface 69 may be, for example, second surface 69 having a second depth 70 from top surface 58; second depth 70 is typically greater than first depth 66. The first depth 66 of first surface 64 and the second depth 70 of second surface 69 in FIG. 3A are shown for illustrative purposes only; however, it is to be understood that, according to aspects of the invention, the second surface 69 may simply be displaced from first surface 64 whereby a step is provided between the two surfaces to provide cavity length 80. This step having cavity length 80 may be provided anywhere about the outside surface, or circumferential surface, of wave guide 52, but is typically provided at a location upon which wave guide 52 impinges the sensing signal, for example, the laser beam. As shown FIGS. 3A and 4, according to aspects of the invention, second surface 69 is provided with a layer 72 from which a diaphragm 73, for example, a circular diaphragm having a diameter 74, may be formed (as will be discussed below), though any shaped diaphragm may be provided according to aspects of the invention, including square, rectangular, or ellipsoidal. During the formation of layer 72, for example, as will be discussed below, one or more other surfaces of substrate 56 may receive a layer of material, for example, the formation of layer 75 on first surface 64.

The size and dimensions shown in FIGS. 3A, 3B, 3C, and 4 are for illustration only and may not reflect the actual relative sizes of the features described. For example, the thickness and diaphragm 73 and the difference in depth, width, or position of surfaces 64 and 69 are illustrated much larger than their actual dimensions according to aspects of the invention, though in some aspects of the invention, the relative sizes shown are smaller than actual dimensions.

Diaphragm 73 typically includes a top surface 76 and a bottom surface 77 and substrate 56 includes at least one cavity 78 that exposes at least a portion of the bottom surface 77 of diaphragm 73, for example, to be accessible to a wave 79 to be detected. As shown in FIGS. 3A and 4, in one aspect, cavity 78 may comprise a hole 78 extending from a bottom surface 59 of substrate 56 to the bottom surface 77 of diaphragm 73. Hole 78 may be circular or non-circular, for example, square, rectangular, or ellipsoidal, and provide access to the wave 79 from a wave source (not shown), for example, an elastic strain wave generated by a fatigue crack, an impact, an inter-surface slippage, twinning, a phase transformations, a plastic deformation, or corrosion fatigue.

FIG. 3A also illustrates several dimensional features of aspects of the invention. For instance, aspects of the invention may include a shift distance 81, a channel or groove angle 82, and a distance from the center 84. These dimensional features may also be applied to sensor 450 in FIG. 3B. As shown in FIG. 3A, shift distance 81 is the distance between the top extremity of the wave-guide 52, for example, an optical fiber, (as indicated by phantom line 83) and the top surface 58 of substrate 56. According to aspects of the invention the value of shift distance 81 may vary broadly, and may be positive or negative. For example, when the value of shift distance 81 is positive, the top extremity of wave guide 52 is above top surface 58 of substrate 56; when the value of shift distance 81 is negative, the top extremity of wave guide 52 is below top surface 58 of substrate 56. According to one aspect of the invention, it can be advantageous to have a positive shift distance whereby the wave-guide 52 extends beyond the surface 58 of substrate 56 where wave-guide 52 can be contacted and firmly compressed to ensure contact between the wave-guide 52 and surface 64 of channel 54. For example, a planar surface, such as, a silicon chip, can be compressed against the exposed wave-guide 52 to ensure contact between wave-guide 52 and surface 64. Shift distance 81 may vary from about −500 μm to about +25 μm, but shift distance 81 typically ranges form about 5 μm to about 15 μm.

Groove angle 82 is the angle that a sidewall of channel 54 makes with the surface 58 of substrate 56. Typically, the groove angle 82 is determined by the crystallographic geometry of the material of substrate 56. For example, for a (100) single crystal silicon substrate, groove angle 82 of grooves along with [110] directions are typically 54.74 degrees, though groove angle 82 will vary for other materials. Groove angle 82 may vary broadly depending upon the substrate material and the etching process used. For example, groove angle 82 can be 90 degree (that is, "U type" groove) when the substrate comprises a (110) silicon wafer and the groove is formed by KOH etching. Also, the groove angle can be about 45 degrees when the substrate comprises fused silica or glass and the groove is formed by an isotropical etching method.

Distance from center 84 is the distance from the centerline of the channel 54, for example, the apex of a V-groove, to the centerline of cavity 78 in substrate 56. Typically, the distance to center 84 will be dependent upon the geometry of channel 54, for example, dependent upon one or more of channel width 60, depth 66, angle of groove 82, cavity length 80, the diameter of wave guide 52. In one aspect of the invention, distance to center 84 is chosen to optimize the location of diagram 73, for example, to locate diaphragm 73 as near as possible to the center of the optical spot projected by the beveled end 57 of wave guide 52 onto diaphragm 73 in order to have the maximum sensitivity. However, according to aspects of the invention, the location of diaphragm 73 may deviate from optimum and still effectively function as described herein.

As shown in FIGS. 3B and 4, sensor 450 includes a waveguide 452, for example, a fiber optic, positioned in an elongated channel, groove, or recess 454 in a substrate 456, for example, in a top surface 458 of substrate 456 having a recess 468. According to the aspect of the invention shown in FIG. 3B, as will be discussed more fully below, the depth of recess 468 in channel 454 providing the second surface may vary while the width 461 of recess 468 may typically be larger than the width 460 of channel 454. As shown most clearly in FIG. 4, wave-guide 452 may typically comprise a beveled end 57, for example, a polished end beveled at anywhere from about 40 to about 50 degrees, for instance, from about 43 to about 47 degrees, but typically beveled at an angle of about 45 degrees. As shown in FIG. 3B, channel 454 has a width 460 at surface 458 and includes a direction of elongation 62, as shown in FIG. 4. Channel 454 provides a first surface 464, for example, at a first depth 466 from surface 458, against which waveguide 452 rests.

As shown in FIG. 3B, according to one aspect of the invention, at least a portion of the first surface 464 of channel 454 may be provided with a recess 468 having a second surface 469 displaced from first surface 464. In one aspect of the invention, the displacement of second surface 469 from first surface 464 may be provided by the second surface 468 having a second depth 470 from top surface 458, greater than first depth 466; however, in contrast to the aspect to the invention shown in FIG. 3A, second depth 470 may vary from first depth 466, as indicated by double arrow 471. For example, second depth 470 may be greater than first depth 466 (for example, as is typical of the aspect shown in FIG. 3A or, for example, providing a bottom surface 467) or substantially equal to or the same as the first depth 466. However, as discussed previously, according to aspects of the invention, the second surface 469 may simply be displaced from first surface 464 whereby a step is provided between the two surfaces to provide cavity length 480. This step having cavity length 480 may be provided anywhere about the outside surface, or circumferential surface, of wave guide 452, but is typically provided at a location upon which wave guide 452 impinges the sensing signal, for example, the laser beam.

According to one aspect of the invention, as shown in FIG. 3B, the relationship between the position of first surface 464 and second surface 469 may be more readily defined by the relative width 461 of recess 468 compared to the width 460 of channel 454. For example, in one aspect, recess 468 and channel 454 may vary in width and thus provide a variation in the relative position of first surface 464 and second surface 469, for example, second surface 469 may be displaced from first surface 464.

As shown FIG. 3B, second surface 469 is provided with a diaphragm 473, for example, a circular diaphragm having a diameter 474, though, as discussed above with respect to diaphragm 73, any shaped diaphragm may be provided according to aspects of the invention, including square, rectangular, or ellipsoidal.

As shown in FIGS. 3C and 4, sensor 550 includes a waveguide 552, for example, a fiber optic, positioned in an elongated channel, groove, or recess 554 having a first surface 564. A recess 568 in channel 554 provides a second surface 569 displaced from first surface 564. According to the aspect of the invention shown in FIG. 3C, and discussed previously, the displacement of second surface 569 from first surface 564 in channel may be established anywhere within channel 554, but is typically provided at a location upon which wave guide 552 impinges the sensing signal, for example, the laser beam. As shown most clearly in FIG. 4, wave-guide 552 may typically comprise a beveled end 57, for example, a polished end beveled at anywhere from about 40 to about 50 degrees, for instance, from about 43 to about 47 degrees, but typically beveled at an angle of about 45 degrees. As shown in FIG. 3B, channel 554 has a width 560 at surface 558. In one aspect, channel 554 provides a first surface 564, for example, at a first depth from surface 558, against which wave-guide 552 rests.

As shown in FIG. 3C, according to one aspect of the invention, at least a portion of the first surface 564 of channel 554 may be provided with a recess 568 having a second surface 569 displaced from first surface 564, for example, having a second depth from top surface 558. As discussed above, according to aspects of the invention, the second surface 569 may simply be displaced from first surface 564 whereby a step is provided between the two surfaces to provide cavity length 580. This step having cavity length 580 may be provided anywhere about the outside surface, or circumferential surface, of wave guide 552, but is typically provided at a location upon which wave guide 552 impinges the sensing signal, for example, the laser beam. As shown FIGS. 3C and 4, according to aspects of the invention, second surface 569 is provided with a diaphragm 573, for example, a circular diaphragm having a diameter 574, though any shaped diaphragm may be provided according to aspects of the invention, including square, rectangular, or ellipsoidal.

However, as shown in FIG. 3C, in contrast to the aspects to the invention shown in FIGS. 3A and 3B, surface 569 may be provided on only a single surface of channel 554. For example, on only one side of a V-shaped channel or groove.

The size and dimensions shown in FIGS. 3A, 3B, 3C, and 4 are for illustration only and may not reflect the actual relative sizes of the features described. For example, the thickness and diameter 74, 474, and 574 of diaphragms 73, 473, and 573, respectably, and the difference in depth, width, and position of surfaces chancels 54, 454, and 545, and recesses 68, 468, respectively, are illustrated much larger than their actual dimensions according to aspects of the invention, though in some aspects, the actual relative dimensions shown may be illustrated much smaller than their actual dimensions.

Similar to diaphragm 73 shown in FIG. 3A, diaphragms 473 and 573 in FIGS. 3B and 3C typically include a top surface and a bottom surface 477, 577 and substrate 456, 556 includes at least one cavity 478, 578 that exposes at least a portion of the bottom surface 477, 577 of diaphragm 473, 573 for example, to be accessible to a wave or stimulus to be detected. As shown in FIGS. 3B and 3C, in aspects of the invention, cavity 478, 578 may comprise a hole extending from a bottom surface 459, 559 of substrate 456, 556 to the bottom surface 477, 577 of diaphragm 473, 573. Hole 478, 578 may be circular or non-circular, for example, square, rectangular, or ellipsoidal, and provide access to the wave or stimulus from a wave source (not shown).

As shown in FIGS. 3A, 3B, 3C, and 4, according to aspects of the invention, the placement of wave-guide 52, 452, 552 along first surface 64, 464, 564 and the providing of second surface 68, 468, 568 having diaphragm 73, 473, 573 provides a well-defined F-P cavity length 80, 480, 580 between the outer surface of wave-guide 52, 452, 552 and diaphragm 73, 473, 573. As discussed above, the accuracy and repeatability of an F-P cavity is highly sensitive to variably of in cavity length 80, 480, 580. However, according to aspects of the invention, cavity length 80, 480, 580 as will be discussed further below, can be closely toleranced during the fabrication process to minimize or eliminate variability of the reflective intensity of the F-P cavity due to variation in cavity length 80, 480, 580.

The operation of sensors 50, 450, and 550 shown in FIGS. 3A, 3B, 3C, and 4 is best illustrated with the aid of FIG. 4. As shown in FIG. 4, a reference signal 90, for example, a reference laser beam having a wavelength λ, for example, a near infrared laser with wavelength of 1.55 µm, is directed along wave-guide 52, 452, 552 and reflects from beveled end 57 as reflected signal 91. According to aspects of the invention, beveled end 57 is positioned adjacent diaphragm 73, 473, 573 for example, superjacent diaphragm 73, 473, 573 whereby reflected beam 91 is directed upon the upper surface 76 of diaphragm 73, 473, 573. At the same time, at least some of the signal 91 reflected from beveled end 57 reflects off the surface of wave-guide 52 as reflected signal or beam 92. Reflected signal 92 is reflected by beveled end 57 and propagates back down wave-guide 52, 452 as reflected signal 93. At least some of signal 91 is transmitted to diaphragm 73, 473, 573 and contacts and reflects from top surface 76 of diaphragm 73 and is reflected as reflected signal 94 and is reflected back along wave-guide 52, 452, 552 as reflected signal 95. According to aspects of the invention, signal 93 reflected from the surface of the wave-guide and the signal 95 reflected from diaphragm 73, 473, 573 interfere with each other, for example, using conventional photo detectors (not shown) and conventional interferometric techniques, to define a characteristic baseline interference pattern for the undeflected or undisturbed diaphragm 73, 473, 573. According to aspects of the invention, the deflection of diaphragm 73, 473, 573 for example, by wave 79, for instance, from an acoustic emission, varies the phase of the reflected signal 95 which can be detected and compared to the baseline interference pattern to determine a characteristic interference pattern for the detected wave 79. However, according to aspects of the invention, the accuracy and repeatability of the initial, baseline phase difference (that is, without stimulus) between signals 93 and 95 can be enhanced due to the improved control and tight tolerances that can be provided for cavity length 80, 480, 580.

Figure 5:
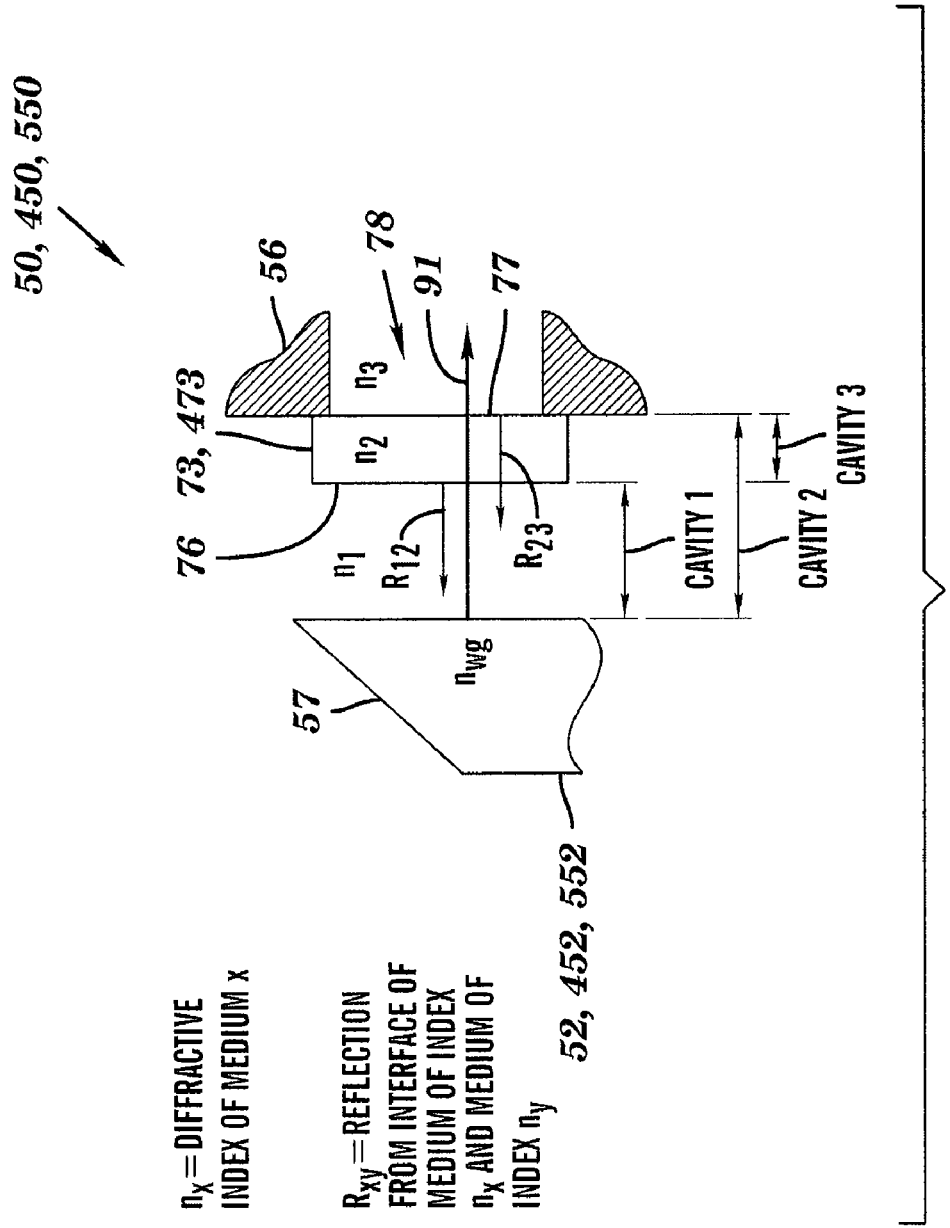
FIG. 5 is a schematic illustration of a portion of the transverse elevation view shown in FIG. 4.

FIG. 5 is a schematic illustration of a portion of the transverse elevation view shown in FIG. 4 including the end of wave-guide 52, 452 having beveled end 57 directing beam 91 upon diaphragm 73 (or diaphragm 473 in FIG. 3B) having a top surface 76 and a bottom surface 77 opposite top surface 76. As shown in FIG. 5, in one aspect, one or more interferometric cavities, that is, a multi-cavity structure, may be provided. For example, as shown in FIG. 5, a interferometric cavity may be provided between the surface of the wave-guide 52 and the top surface 76 of diaphragm 73 (that is, "Cavity 1"); between the surface of the wave-guide 52 and the bottom surface 77 of diaphragm 73 ("Cavity 2"); and/or between the top surface 77 of diaphragm 73 and the bottom surface 77 of diaphragm 73 ("Cavity 3"). According to aspects of the invention, one or more of these cavities may be utilized in detecting the stimulus. For example, in one aspect, cavity 1 or cavity 2 or both cavity 1 and cavity 2 may be used for an interferometric or F-P cavity.

In one aspect, the surface defining the length of the interferometric cavity length may be a function of the media, for example, air, water, an oil, etc., surrounding the sensor. For example, the refractive index, n, of the medium contacting the wave-guide 52, top surface 76 of diaphragm 73, and bottom surface 77 of diaphragm 73 may impact the reflectivity of the electromagnetic signal from the interface and thus affect the strength (for example, energy) of the reflected signal. This is illustrated schematically in FIG. 5.

For example, when diaphragm 73 is not coated, for example, not coated with a metal surface, and diaphragm 73 is substantially transparent, the optical refractive index between wave-guide 52 and diaphragm 73 may be designated $n_1$; the refractive index of diaphragm 73, $n_2$; and the refractive index of the medium in the aperture 78, $n_3$. Then, as is known in the art, the intensity of the reflected radiation, $R_{xy}$, reflected from the interface at the top 76 of diaphragm 73, $R_{12}$, and at the bottom 77 of diaphragm 73, $R_{23}$, are provided by the relationships in Equation 2 below:

$$R_{12}=[(n_2-n_1)/(n_1+n_2)]^2 \text{ and } R_{23}=[(n_2-n_3)/(n_3+n_2)]^2 \qquad \text{Equation 2.}$$

According to these relationships, if adjacent media have similar refraction indices, $n_{xy}$, the reflection, $R_{xy}$, will be smaller, for example, smaller than the reflection from an interface having different or dissimilar refractive indices.

For example, in one aspect of the invention, sensor 50, 450 may be immersed in an oil, for example, in a transformer having an oil, having an index $n_1=1.47$; the diaphragm 73 may be silicon dioxide having an index $n_2=1.45$, and the aperture 78 may be sealed and contain air having a refractive index $n_3=1.0$. From the above relationships in Equation 2, due to the similarity of $n_1$ and $n_2$, $R_{12}$ will be relatively less than $R_{23}$, whereby the bottom surface 77 of diaphragm 73 will be more effective as a reflection surface for an interferometric cavity.

Note that in some aspects of the invention, should the reflection $R_{xy}$ be insufficient, the top 76 or bottom 77 of diaphragm 73 and/or the surface of the wave-guide 52 may be coated with a reflection enhancing material, for example, a metal, to provide the desired reflectivity. In one aspect, should the refractive index of the wave-guide, $n_{wg}$, approach the refractive index of the medium surrounding the wave-guide, $n_1$, the wave-guide 52 may be coated to provide the desired reflection.

Figure 6:
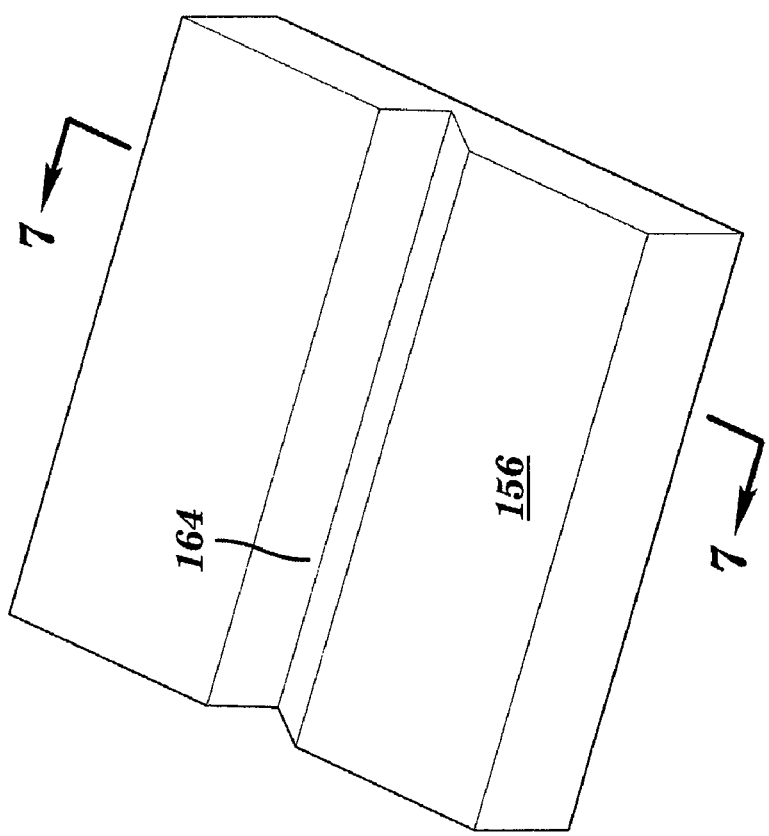
FIGS. 6, 7, and 8, are a perspective view, a cross-sectional view, and a plan view, respectively, of a channel in a substrate according to an aspect of the invention.
Figure 7:
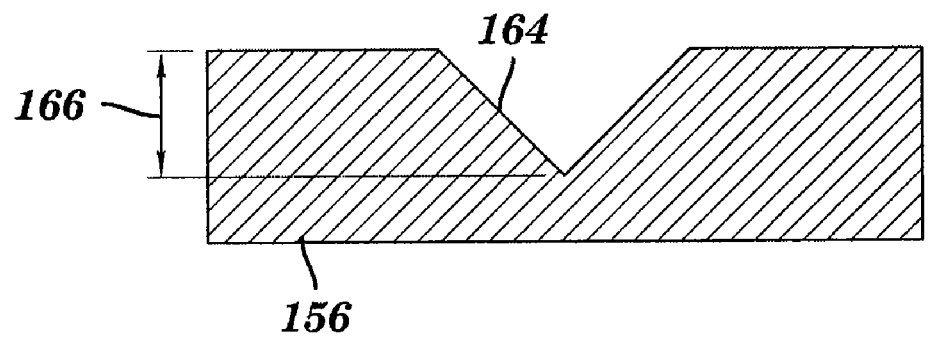
Figure 8:
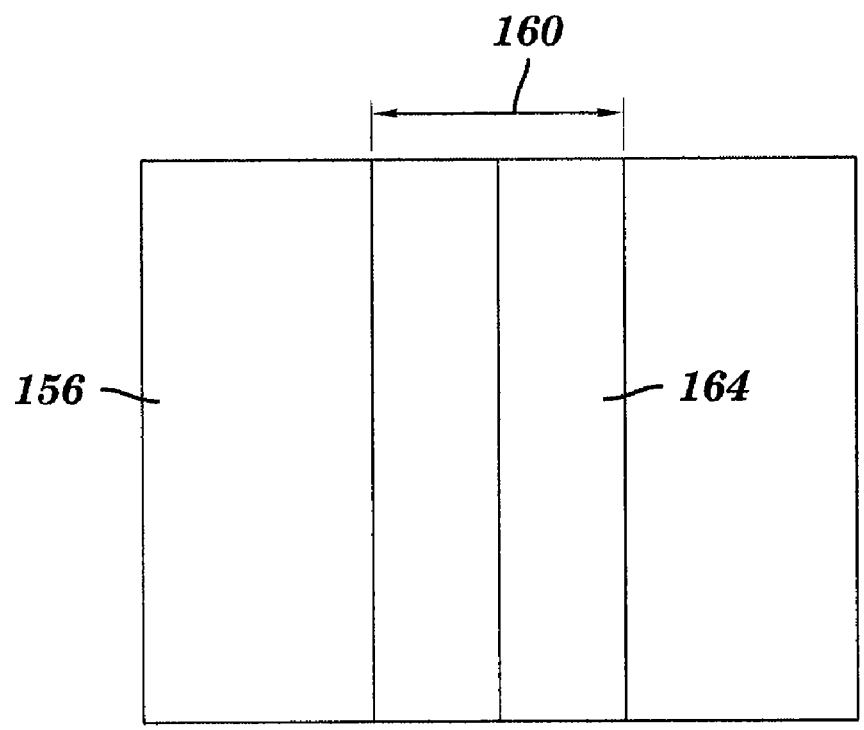

FIGS. 6 through 20 illustrate methods of fabricating a sensor, for example, a sensor similar to sensor 50, 450, 550 according to aspects of the invention. FIGS. 6, 7, and 8 are a perspective view, a cross-sectional view, and a plan view, respectively, of a channel, groove, or recess 164, for example, an elongated channel, in a substrate 156 according to one aspect of the invention. The cross-section shown in FIG. 7 is as viewed through section 7-7 shown in FIG. 6. In this and the following discussion reference numbers preceded by the numeral "1" may correspond to items and structures identified without the numeral "1" or with the numeral "4" or with the numeral "5" in FIGS. 1-5 and described with respect to FIGS. 1-5 above.

Substrate 156 may be made from any conventional material, for example, a metal, a metalloid, or a plastic. In one aspect of the invention, substrate 156 is a material that is conducive to conventional photolithographic or MEMS (Micro-Electrical-Mechanical Systems)-type processing, for example, wet etching, thin film deposition, and deep etching, among other processes. For example, in one aspect, substrate 156 may be made from silicon (Si), for example, single-crystal silicon. Prior to the formation of channel 164, when channel 164 is formed by etching, the substrate 156 may be coated with silicon oxide or silicon nitride and photolithographed to open the anisotropic wet etching window in preparation for etching, as is conventional.

Etching, for example, wet anisotropic wet etching, of a silicon wafer is sensitive to defects in the substrate 156, for example, defects in the single crystal silicon substrate. For example, it has been found that the etching rate around a defect is higher than that at other places in the substrate. Accordingly, it is preferred that high quality substrates be used for aspects of the invention. However, high temperature processing, such as, thermal oxidization, can introduce defects inside the substrate. Therefore, in one aspect of the invention, the mask layer for the etching process, for example, for KOH etching, may be a mask fabricated by a lower temperature CVD process, that is, compared to the temperature of thermal silicon dioxide mask fabrication. For example, a silicon nitride mask fabricated by a lower temperature LPCVD process may be used. The LPCVD process temperature is much lower than that of thermal oxidization, and can thus be less likely to introduce defects to the substrate that can typically be introduced by thermal oxidation processes, for example, the thermal oxidation of silicon dioxide.

Channel 164 may assume many different shapes according to aspects of the invention, for example, having a square, rectangular, polygonal, circular, semi-circular, u-shaped, v-shaped, or oval cross section, among other cross-sectional shapes. In one aspect of the invention, as shown most clearly in FIG. 7, channel 164 may have a triangular cross section with an apex directed into substrate 156, that is, a "V groove" in the surface of substrate 156. In one aspect, channel 164 may comprise a cross section having at least one sidewall, for example, one vertical or inclined wall onto which a diaphragm can be formed and through which an aperture can be provided. In one aspect, the channel may have V-shaped cross-section with a substantially horizontal base, for example, at the bottom of the channel.

However, according to aspects of the invention, as will become more apparent in the discussion below, the shape of channel 164 may assume any shape that this conducive to the shape of and optical properties of the wave guide positioned in channel 164.

Channel 164 may have a width 160 ranging from about 100 μm to about 1500 μm, and typically may have a width 160 of about 200 μm to about 400 μm. Depth 166 will vary according to width 160 due to the crystal angle of the substrate, for example, the relatively fixed angle of a silicon (100) wafer, as discussed above. Channel width 160 is determined by, among other things, the thickness of the substrate 156, for example, the thicker the substrate wafer, the larger width 160 may be. However, it is to be understood that it is not necessary to etch down to an apex of a V or U shape, as shown in FIG. 3B. In one aspect, the minimum width 160 and depth 166 are those dimensions that permit the wave-guide for example, the optical fiber (as discussed below), to settle into and firmly contact and be supported by the surfaces of the channel, for example, the two side surfaces of a V-shaped channel.

Channel 164 may be formed by any conventional forming process, for example, by conventional machining. However, in one aspect of the invention, channel 164 may be formed by one or more photolithographic or MEMS-type processing methods, for example, anisotropic wet etching or deep etching, among other methods.

In one aspect of the invention, channel 164 comprises a "V-groove" in the surface of substrate 156. The inventors have found that when the wave-guide used comprises a standard, circular cylindrical shaped optical fiber, the V-groove shape of channel 164 is a preferred structure to hold the standard optical fiber. In one aspect, the channel 164, regardless of shape, serves as the frame structure of the sensor. When substrate 156 comprises a silicon substrate, channel 164, for example, a V-groove channel, may typically be fabricated by wet anisotropic etching on the (100) plane of the silicon substrate. The position, depth, and width of channel 164 may primarily be determined by the material removal method used, for example, by photolithography and wet anisotropic etching.

Figure 9:
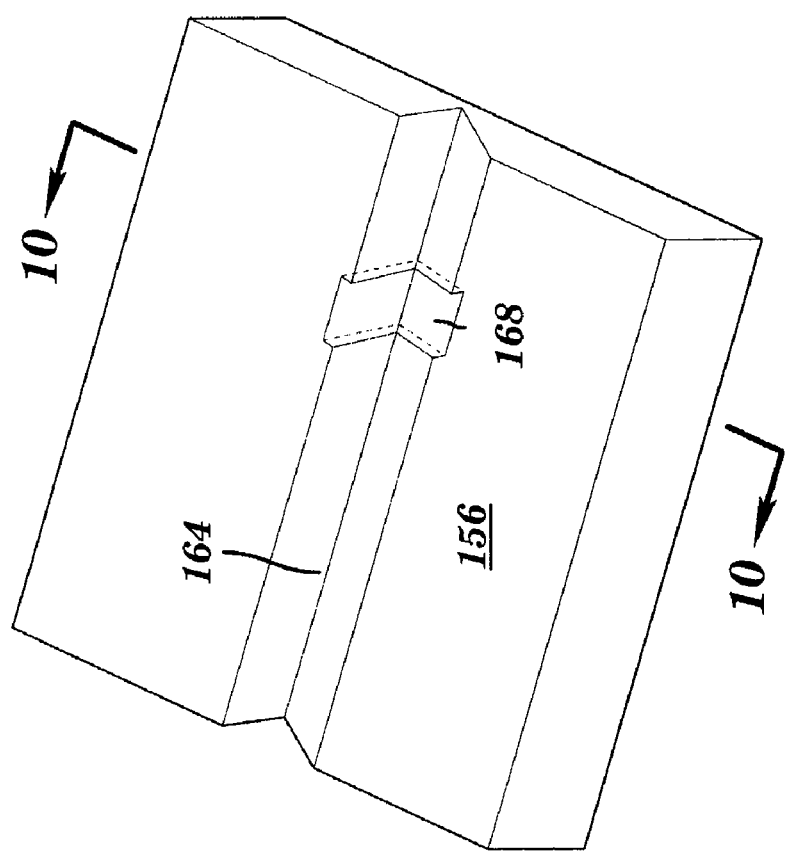
FIGS. 9, 10, and 11, are a perspective view, a cross-sectional view, and a plan view, respectively, of the channel shown in FIGS. 6, 7, and 8, respectively, having a recess according to an aspect of the invention.
Figure 10:
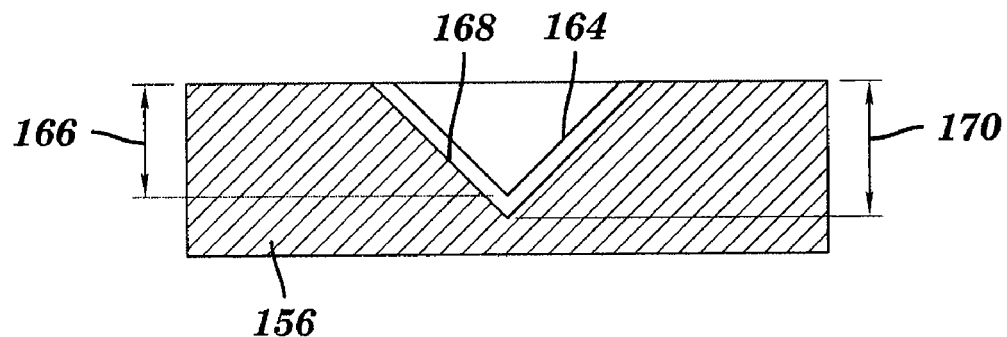
Figure 11:
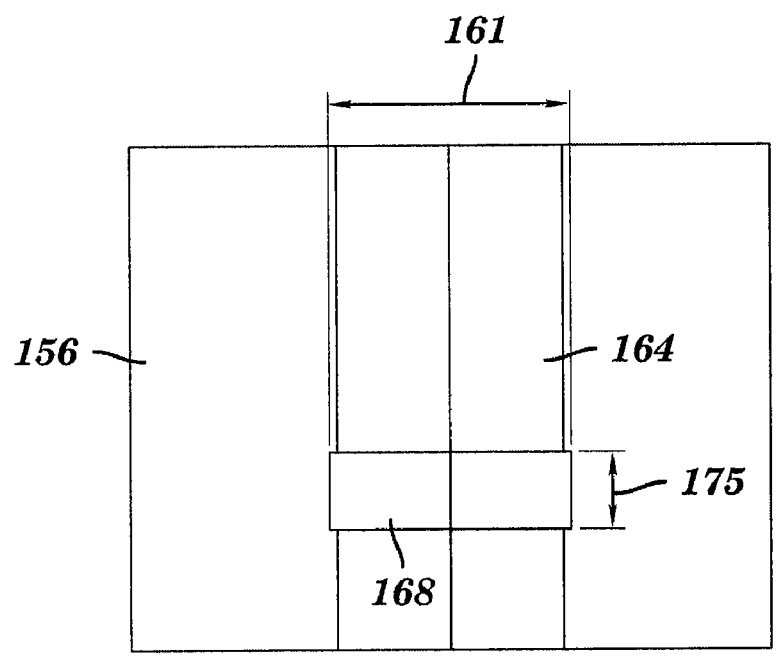

FIGS. 9, 10, and 11, are a perspective view, a cross-sectional view, and a plan view, respectively, of the channel, groove, or recess 164 shown in FIGS. 6, 7, and 8, respectively, having a recess 168 according to an aspect of the invention. The cross-section shown in FIG. 10 is as viewed through section 10-10 shown in FIG. 9. It is to be understood that though recess 168 shown in FIGS. 9 through 20 is similar to recess 68 shown in FIG. 3A, recess 168 may also be similar in structure to recess 468 or 568 shown in FIGS. 3B and 3C. In one aspect of the invention, recess 168 may be formed at substantially the same time as channel 164, for example, in the same etching process.

Recess 168 may assume many different shapes according to aspects of the invention, for example, having a square, rectangular, polygonal, circular, or oval cross section. In one aspect of the invention, as shown most clearly in FIG. 10, recess 168 may be similar in shape to channel 164 and have a triangular cross section with an apex directed into substrate 156, that is, again, a V-groove similar to channel 164. However, according to aspects of the invention, as will become more apparent in the discussion below, the shape of channel 168 may assume any shape that this conducive to the shape of and optical properties of the wave guide positioned in channel 164 above recess 168. In addition, according to aspects of the invention, regardless of the shapes of channel 164 and recess 168, the difference in the size and/or position of at least one of the side walls of channel 164 and the size and/or position of at least one of the sidewalls of recess 168 may define the F-P cavity length between the optical fiber and the diaphragm fabricated on the sidewall of recess 168.

Recess 168 may also be formed by any conventional forming process, for example, by conventional machining. However, in one aspect of the invention, recess 168 may be formed by one or more photolithographic or MEMS-type processing methods described with respect to channel 164 above, for example, anisotropic wet etching or deep etching, among other methods.

Recess 168 may have a first width 161 and a second width 175. First width 161 may vary broadly depending upon the width 160 and position of channel 164 and the F-P cavity length 180, among other things. In one aspect, first width 161 may vary from about 100 μm to about 2000 μm, and typically width 161 may vary from about 200 μm to about 500 μm. Second width 175 may range from about 50 μm to about 5000 μm, and typically second width 175 may range from about 200 μm to about 400 μm. Depth 170 will vary according to width 161 due to the crystal angle of the substrate, for example, the relatively fixed angle of a silicon (100) wafer, as discussed above.

In one aspect of the invention, channel 164 and recess 168 may both comprises V-grooves with two different widths. The V-groove a channel 164 may be used to accommodate an optical fiber, for example, a standard, circular cylindrical optical fiber, and the V-groove of recess 168 may be used as a platform to fabricate a thin diaphragm on its sidewall, as will be discussed below. Again, according to aspects of the invention, the difference in the size and/or position of the side walls of the V-groove of channel 164 and the sidewalls of V-groove of recess 168 may define the F-P cavity length between the optical fiber and the diaphragm fabricated on the sidewall of the V-groove of recess 168.

When the wave-guide is a circular cylindrical optical fiber, the position of the optical fiber outer surface or sidewall is determined by the sidewall of the V-groove of channel 164 that holds the optical fiber. Consequently, in one aspect, the size and/or position of the V-groove of channel 164 and the size and/or position of V-groove of recess 168 determine the cavity length, L. In one aspect, when the channel 164 and recess 168 are formed by photolithographic methods, the sizes and positions of the V-grooves of channel 164 and of recess 168 are determined by the etching window. As a result, the size and/or position of the V-groove of channel 164 and the size and/or position of V-groove of recess 168 can be positioned and sized with enhanced accuracy, for example, with the accuracy of photolithography. For example, in one aspect, the size and/or position of the V-groove of channel 164 and the size and/or position of V-groove of recess 168 may be within several nanometers, for instance, +/−5 to 10 nanometers, or less. Accordingly, the size of the cavity lengths of the F-P cavity that can be provided when employing aspects of the present invention may be controlled within several nanometers, for instance, +/−5 to 10 nanometers, or less. That is, cavity length accuracies can be obtained by aspects of the invention that cannot be obtained by prior art methods, especially, not with the diaphragm thicknesses (and inherent AE sensing sensitivities) achievable with aspects of the invention.

Figure 12:
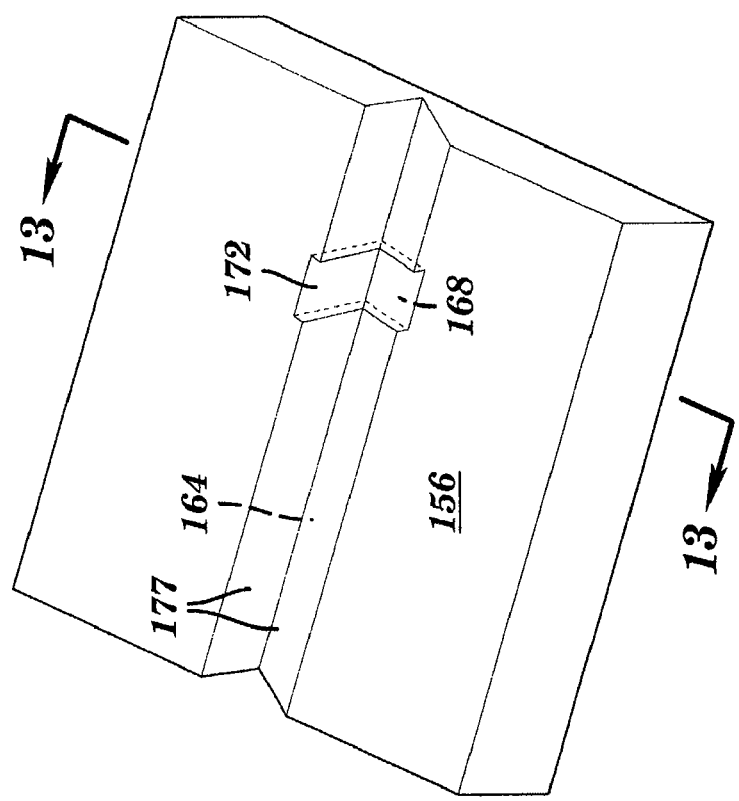
FIGS. 12, 13, and 14, are a perspective view, a cross-sectional view, and a plan view, respectively, of the recess shown in FIGS. 9, 10, and 11, respectively, having a diaphragm according to an aspect of the invention.
Figure 13:
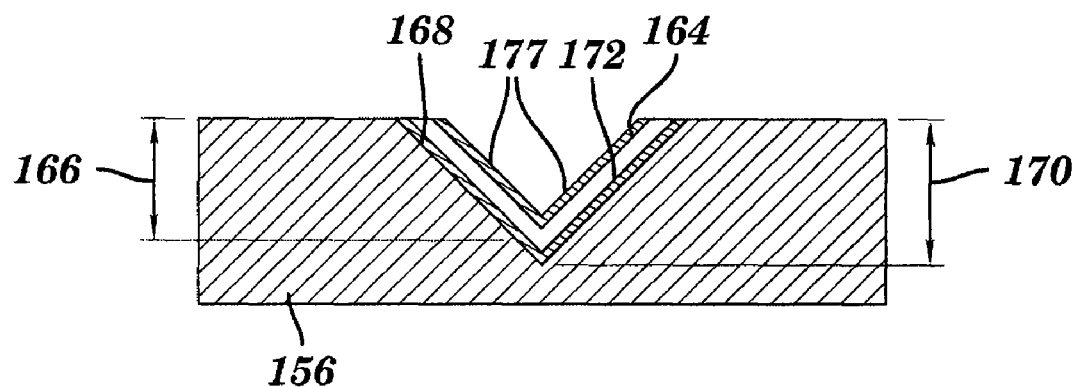
Figure 14:
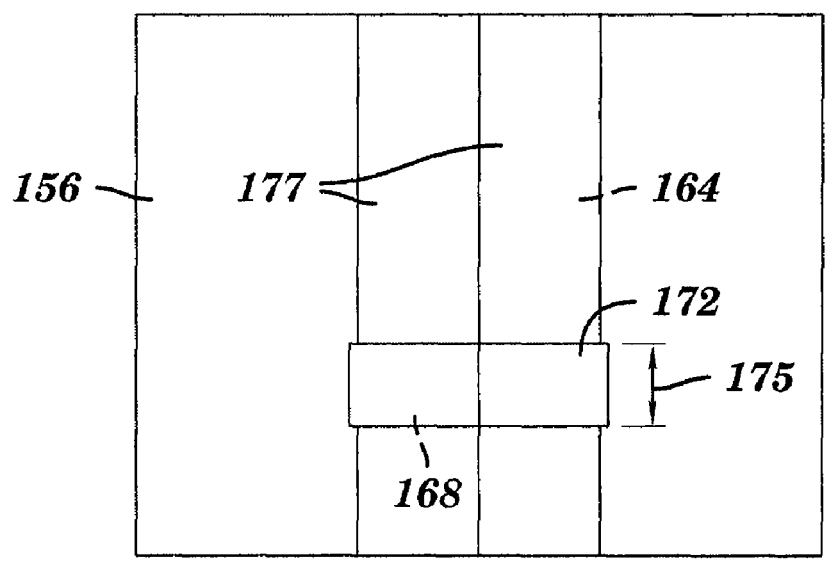

FIGS. 12, 13, and 14, are a perspective view, a cross-sectional view, and a plan view, respectively, of the recess 168 in channel 164 shown in FIGS. 9, 10, and 11, respectively, having a layer 172 from which a diaphragm can be formed according to one aspect of the invention. The cross-section shown in FIG. 13 is as viewed through section 13-13 shown in FIG. 12.

Layer 172 may comprise a thin film, for example, a thin layer having a thickness less than or equal to about 10 micrometers, or less than or equal to about 1.0 micrometer, for example, between about 0.2 micrometers and about 1.0 micrometers. However, in some aspects of the invention, the layer thickness may be less than about 0.2 micrometers, for example, between about 0.05 to about 0.2 micrometers, though in some aspects, the layer may have a thickness less than about 0.05 micrometers (that is, less than or equal to 50 nanometers). Layer 172 typically covers surface at least some of the surface of recess 168, for example, at least one of the surfaces of a V-groove recess 168. In one aspect, layer 172 may cover substantially the entire surface of recess 168 and the entire surface of channel 164, for example, both surfaces of a v-groove surface and all surfaces of channel 164, as indicated by layer 177 in FIGS. 13-14.

The inventors recognize, however, the thickness of the layer 172 may be limited by the structural integrity of the resulting diaphragm, as will be discussed below, which can be more fragile as diaphragm thickness decreases. In some aspects of the invention, not only a more repeatable and more reliable sensor is provided, but also a sensor with enhanced sensitivity due to the thinner diaphragm than can be provided in the prior art.

The relative size of layer 172, and other features, shown in FIGS. 12-14, as well as in other figures herein, is not to scale, but is enlarged to facilitate illustration of aspects of the invention.

Layer 172 may be formed by depositing a material on the surface of recess 168 in channel 164, for example, by growing or depositing one or more layers of polymeric material, for example, a multilayer diaphragm. Layer 172 may be formed by any conventional thin layer or diaphragm forming process, for example, by conventional means of applying a thin layer to the surface of recess 168. However, in one aspect of the invention, layer 172 may be formed by one or more photolithographic or MEMS-type processing methods, for example, a depositing process, for instance, a vapor deposition process (VDP), a low-pressure chemical vapor deposition (LPCVD) process, an atmospheric pressure chemical vapor deposition (APCVD) process, a high-vacuum chemical vapor deposition (HVCVD), or a plasma-enhanced chemical vapor deposition (PECVD), among other methods. In one aspect, a LPCVD process may be used to deposit silicon nitride on recess 168. The inventors have found that LPCVD-deposited silicon nitride has preferential etching qualities compared to other materials present. For example, when silicon dioxide is present (as will be discussed below with respect to the aspect of the invention described in FIGS. 24-26), LPCVD-deposited silicon nitride is removed during etching, for example, with a buffered oxide etchant (BOE) or hydrofluoric acid (HF), at a slower rate than the removal of silicon dioxide. Therefore, in one aspect of the invention, layer 172 may be deposited by a LPCVD process in order to facilitate exposure of the bottom surface of layer 172 at a later time to form a diaphragm. The inventors have also found that an LPCVD process can fabricate silicon nitride with better mechanical properties, for example, with lower pinhole density.

Layer 172 may be made from any material conducive to one or more the deposition processes listed above, for example, in one aspect, layer 172 may be made from a silicon nitride. Layer 172 may be a metal, for example, copper or aluminum; an alloy, for example, a chromium (Cr)/copper (Cu) alloy; a polymer, for example, a poly (methyl methacrylate) (PMMA) or its equivalent; a semiconductor material, such as, silicon or polysilicon; a dielectric material, for example, silicon dioxide ($SiO_2$) or a silicon nitride; or a combination of two or more of these materials.

It will be understood by those of skill in the art that the expression "silicon nitride" is not limited to the material having the chemical formula $Si_3N_4$, but may include similar materials containing silicon and nitrogen. For example, one material that may be used for the layer may comprise a silicon nitride grown by PECVD and having at least some hydrogen in addition to the silicon and nitrogen. In one aspect, the material for the layer 172 may comprise materials that may not strictly adhere to the 3:4 ratio indicative of the formula $Si_3N_4$, for example, silicon and nitrogen containing materials having their composition varied in order to adjust the stress field in layer 172 and/or optical properties (such as, refractive index) of the material, such as, the presence of oxygen. For example, thermal gradients that may be generated during and after fabrication may cause stresses in layer 172 and in the subsequent diaphragm due to, for example, variation in thermal expansion coefficients of the mating materials. Varying the content of layer 172 may vary the expansion coefficient of layer 172 such that these stresses may be reduced.

Layer 172 may be, translucent, transparent, opaque, or at least partially reflective. For example, Layer 172 may comprise and at least partially transparent silicon dioxide or silicon nitride, and/or the top or bottom surface of layer 172 may comprise a thin metal layer, for example, a reflective thin metal layer, for instance, a sputtered gold layer.

In one aspect of the invention, prior to depositing layer 172 unto the surface of recess 168, a dielectric material may be applied to the surface of recess 168 to act as an etching stop layer beneath layer 172 during subsequent processing, for example, during etching of a cavity beneath diaphragm 173, as discussed below. For instance, a thin layer of dielectric, such as, a silicon oxide layer or a silicon nitride layer grown by PECVD, may be applied to the surface of recess 168 to function as an etching stop layer.

Figure 15:
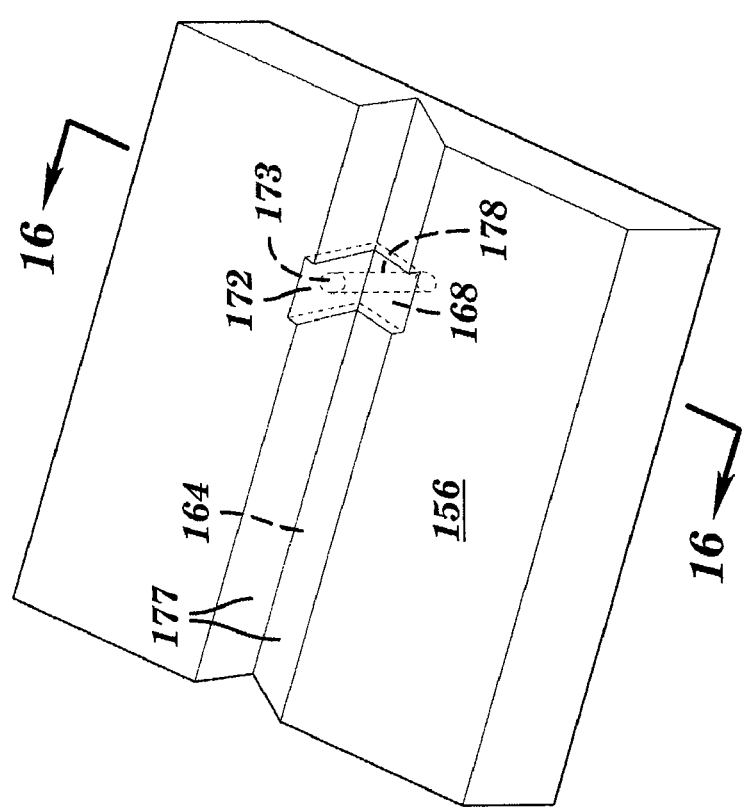
FIGS. 15, 16, and 17, are a perspective view, a cross-sectional view, and a plan view, respectively, of the recess shown in FIGS. 12, 13, and 14, respectively, having a cavity beneath the diaphragm according to an aspect of the invention.
Figure 16:
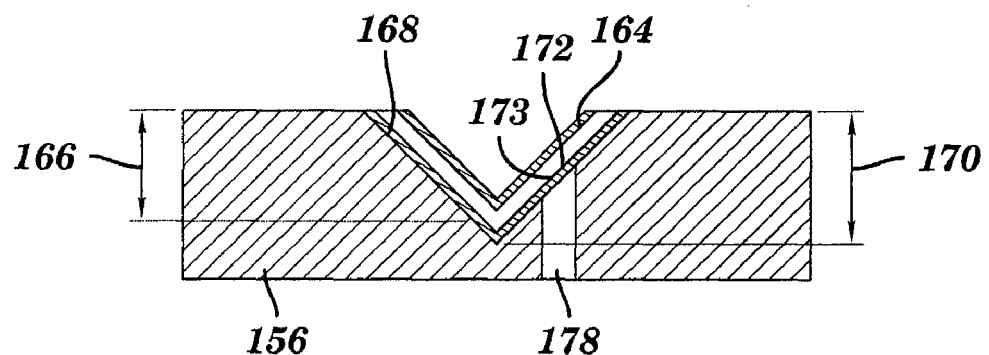
Figure 17:
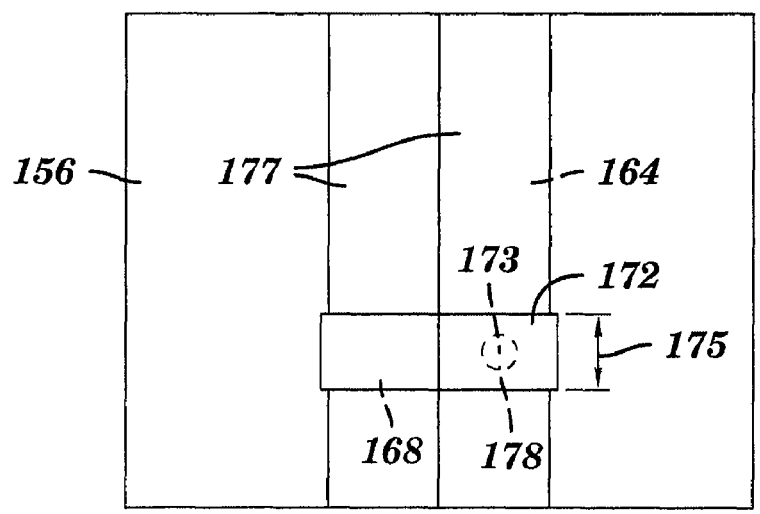

FIGS. 15, 16, and 17, are a perspective view, a cross-sectional view, and a plan view, respectively, of recess 168 and layer 172 shown in FIGS. 12, 13, and 14, respectively, having a cavity or hole 178 beneath the layer 172 according to one aspect of the invention whereby a diaphragm 173 is "released." The cross-section shown in FIG. 16 is as viewed through section 16-16 shown in FIG. 15.

According to aspects of the invention, any process may be used to remove at least some material from beneath layer 172 to provide a diaphragm 173 in layer 172, for example, to "release the diaphragm" 173 from the surrounding substrate 156. According to aspects of the invention, the released diaphragm 173 can have a surface that may be exposed to a stimulus, for example, an AE wave, whereby diaphragm 173 is deflected. Cavity 178 may be formed in substrate 156 by conventional processes, for example, by milling or drilling of substrate 156. However, in one aspect of the invention cavity 178 may be formed by one or more photolithographic or MEMS-type processing methods, for example, an etching process, for instance, an anisotropic wet etching process, an isotropic wet etching process, an anisotropic dry etching process, or an isotropic dry etching process, among other methods. In one aspect, cavity 178 may be formed by wet anisotropic etching where the etchant may be a buffered oxide etchant (BOE) or hydrofluoric acid (HF). For example, a 49% concentration of HF may be used. In another aspect, a dry anisotropic etching, for example, Inductively Coupled Plasma Reactive Ion Etching (ICP-RIE), may be used. One preferred etching process is illustrated and described with respect to FIGS. 24, 25, and 26 below.

Cavity 178 and, consequently, diaphragm 173 may have many different cross sectional shapes according to aspects of the invention, for example, having a square, rectangular, polygonal, circular, semi-circular, or oval cross section, among other cross-sectional shapes. The width or outside diameter and depth of cavity 178 and the outside dimension of diaphragm 173 may vary broadly depending upon the method used to produce it. For example, when cavity 178 is produced by the ICP-RIE method, the shape of cavity 178 may be an ellipse having a projection on surface 168 of a circle defining the diameter diaphragm 173. The resulting diameter of diaphragm 173 may range from about 10 μm to about 300 μm, and typically may range form as a width or outside diameter of about 20 μm to about 100 μm. The relative size of cavity 178 shown in FIGS. 15-17, as well as in other figures herein, is not to scale, but is enlarged to facilitate illustration of aspects of the invention.

Figure 18:
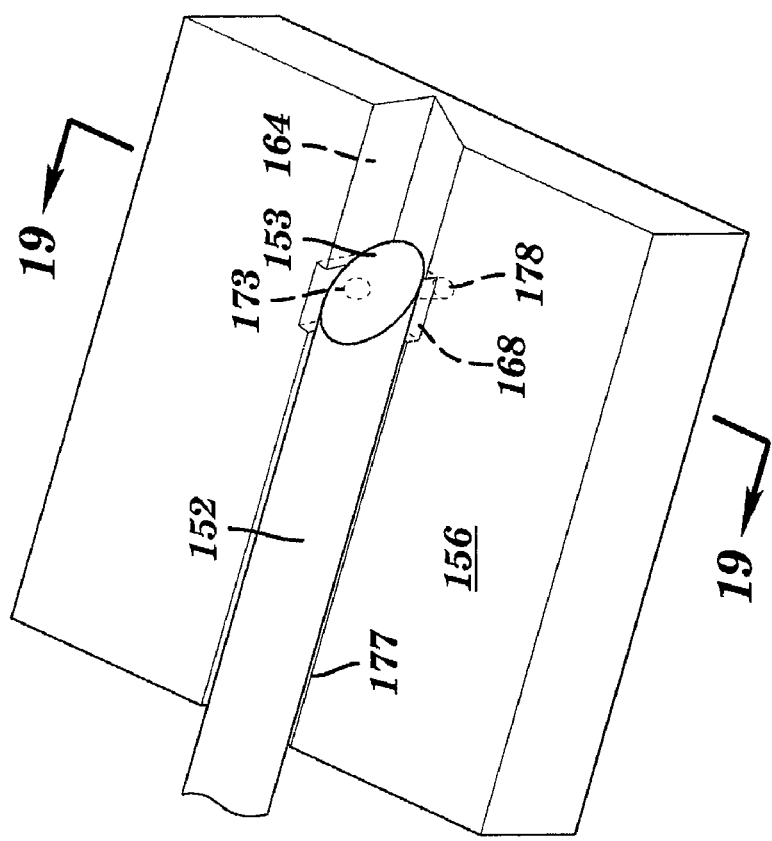
FIGS. 18, 19, and 20, are a perspective view, a cross-sectional view, and a plan view, respectively, of the groove shown in FIGS. 15, 16, and 17, respectively, having a wave guide positioned in the groove according to an aspect of the invention.
Figure 19:
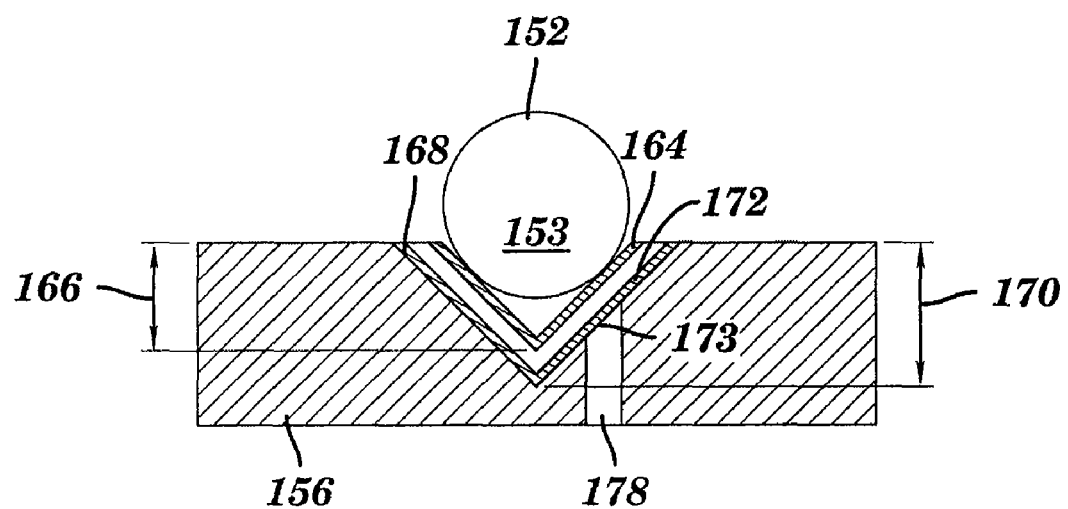
Figure 20:
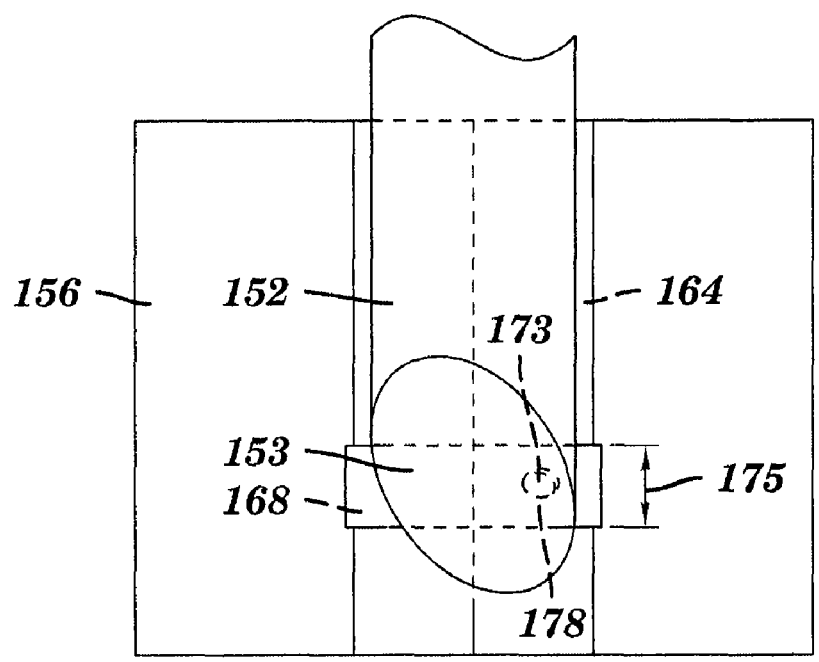

FIGS. 18, 19, and 20, are a perspective view, a cross-sectional view, and a plan view, respectively, of the groove 164 shown in FIGS. 15, 16, and 17, respectively, having a wave-guide 152 positioned in the groove 164 according to one aspect of the invention. The cross-section shown in FIG. 19 is as viewed through section 19-19 shown in FIG. 18. FIGS. 18, 19, and 20 illustrate a typical complete sensor assembly according to aspects of the invention.

Wave-guide 152 may be any conventional wave-guide adapted to transmit an electromagnetic beam or wave and direct it upon diaphragm 173. The electromagnetic beam or wave transmitted by wave-guide 152 from a source (not shown) may comprise any form of electromagnetic radiation that can be directed along a wave-guide, including microwaves, T-rays, infrared light, visible light, ultraviolet light, X-Rays, gamma rays, or radio waves. However, in one aspect, the beam or waves transmitted by wave-guide 152 comprise a laser, for example, a near infrared laser with wavelength of 1.55 um.

In one aspect, wave-guide 152 comprises an optical fiber, for example, a conventional optical fiber having a circular cylindrical shape and a circular cross section. Wave-guide 152 may be a single-mode or a multimode optical fiber. In one aspect, wave-guide 152 may be a SMF-28 single mode optical fiber provided by Corning Inc., or its equivalent. Wave-guide 152 may be coated, for example, coated to vary the reflectivity of the wave-guide.

According to aspects of the invention, wave-guide 152 may be a an optical fiber having a end 153 that is beveled at an angle, for example, beveled and polished, whereby a beam or wave transmitted along wave-guide 152 is reflected from end 153 upon diaphragm 173. The angle of the beveled end 153 of wave-guide 152 may vary from about 40 degrees to about 50, for example, about 45 degrees, to the axis of wave-guide 152, that is, depending upon the relative location of the beveled end 153 to the diaphragm 173. However, in one aspect of the invention, diaphragm 173 is positioned substantially beneath beveled end 153 whereby the angle of beveled end 153 is about 45 degrees to the axis of wave-guide 152 whereby beveled end 153 transmits light to and receives light from diaphragm 173.

The outside diameter or sidewall of optical fiber wave-guide 152 typically contacts, for example, firmly contacts, the sidewall of channel 164. According to aspects of the invention, as shown in FIG. 5, the sidewall of wave-guide 152 may define the boundary of a F-B cavity.

FIGS. 21, 22, and 23 illustrate three perspective views of an EFPI sensor 250 fabricated according to aspects of the invention. FIG. 21 is a perspective view, similar to FIG. 18, of sensor 250. FIG. 22 is a perspective view, partially in cross section of sensor 250 shown in FIG. 21 and FIG. 23 is a plan view of sensor 250 shown in FIG. 21. Similar to the aspect of the invention shown in FIGS. 3-20, sensor 250 shown in FIGS. 21-23, includes a substrate 256, for example, a silicon substrate; a channel 264 in substrate 256; a recess 268 in channel 264; a layer 272, for example, a silicon nitride diaphragm, positioned in recess 268; a cavity 278 in substrate 256 beneath layer 272 forming diaphragm 273; and a wave-guide 252, for example, a fiber optic, having a beveled end 253 positioned in channel 264 whereby beveled end 253 is positioned over diaphragm 273. The features and aspects of sensor 250 are similar to, if not identical to, the features of the corresponding structures shown in FIGS. 3-20 but identified without the preceding numeral "2" or having the preceding numeral "1" or "4" or "5" instead of the preceding numeral "2."

Figure 26:
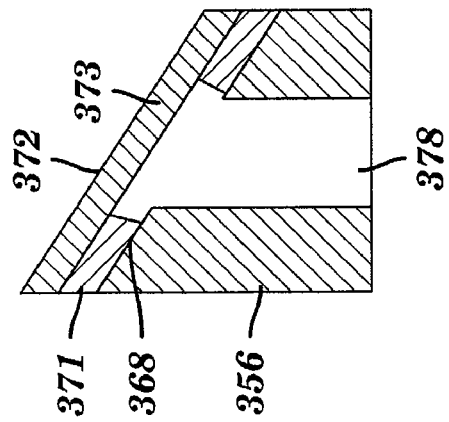
FIGS. 24, 25, and 26 illustrate steps in a method of providing a cavity beneath a diaphragm according to an aspect of the invention.
Figure 25:
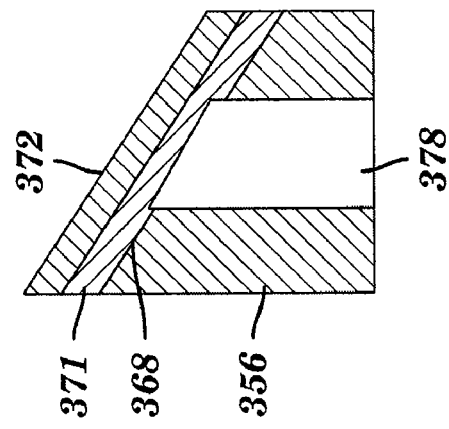
Figure 24:
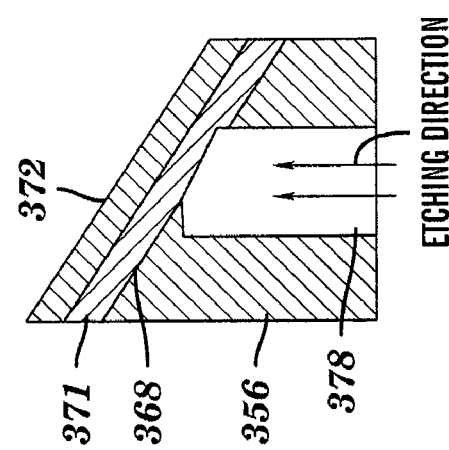

FIGS. 24, 25, and 26 illustrate steps in a method of providing a cavity beneath the diaphragm according to one aspect of the invention. As shown in FIGS. 16, 19, and 22 above, due to the orientation of the surface of recess 168, 268, the axis of cavity 178, 278 in substrate 156, 256 beneath layer 172, 272 may typically form an angle with the plane of the surface of recess 168, 268. Accordingly, the use of conventional material removal processes, for example, anisotropic etching, can result in undesirable, non-uniform thicknesses of diaphragms 173, 273 formed in layer 172, 272. The processes shown in FIGS. 24-26 addresses this issue.

FIG. 24 illustrates a section of a substrate 356, for example, a single-crystal silicon substrate, having a representative surface 368 of a channel, such as, channel 168 or 268 above. Upon surface 368 is deposited a first material 371, for example, a silicon dioxide, and then a second material 372, for example, a silicon nitride. According to aspects of the invention, the materials 371 and/or 372 may be used to form a diaphragm, such as diaphragm 173, 273 disclosed above, beneath which a cavity 378 is formed to expose at least a portion of the deposited materials 371 and/or 372 to provide a diaphragm 373 according to aspects of the invention. Materials 371 and 372 may be deposited on substrate 356 by any one or more of the conventional deposition methods mentioned above. As shown in FIG. 24, because the orientation of the surface 368 of the recess 378 is not perpendicular to the orientation of the surface 368 of substrate 356, for example, a silicon wafer, and because the material of substrate 356 and first material 371 may typically not respond at the same rate to the material removal process, for example, etching, the depth of cavity 378 may vary due to the material removal process, as shown. As shown in FIG. 25, an etching process, for example, dry anisotropic etching process, may not remove material from material 371 at the same rate as substrate 356, but as a result, the removal process may remove only a portion of first material 371. As a result, the uneven removal of first material 371, if not addressed, may typically result in a non-uniform thickness in the diaphragm comprising the remaining portions of first material 371 and second material 372.

Since a non-uniform diaphragm thickness is undesirable, according to one aspect of the invention, the first material 371 is first deposited before second material 372 where first material 371 has an material removal rate that is different, for example, greater than, the second material 372. For example, first material 371 may be a silicon dioxide and second material 372 may be a silicon nitride. In other words, according to aspects of the invention, first material 371 acts as a "buffer layer," for example, protecting the second material 372 from the material removal process.

As shown in FIGS. 25 and 26, after a first material removal step, for example, dry anisotropic etching, removes the material of substrate 356, for example, a silicon, and at least some of first material 371, for example, a silicon dioxide, a second material removal step removes first material 371 to expose at least a portion of second material 372, while removing little or none of second material 372, to provide a substantially uniform diaphragm 373 of second material 372. In one aspect, the second material removal process may be an etching process employing hydrofluoric acid (HF). The removal rate of silicon dioxide 371 is greater with HF etching than the removal rate of silicon nitride 372 with HF. According to an aspect of the invention, the HF etching process removes first material 371 to yield a second material 372 of substantially uniform thickness to provide a diaphragm 373 of substantially uniform thickness on the surface 368. In one aspect, second material 372 may be a silicon nitride produced by a LPCVD process, though a silicon nitride produced by a PECVD process may also be used.

According to another aspects of the invention, the accuracy of the etching process may be enhanced by what is known in the art as "salient compensation" or "convex corner compensation." For example, as described by Chu and Fang in "A Novel Convex Corner Compensation for Wet Anisotropic Etching on (100) Silicon Wafer," *Micro Electro Mechanical Systems*, 2004, 17th IEEE International Conference on MEMS, (2004), pp. 253-256 (the disclosure of which is incorporated by reference herein in its entirety), various methods are disclosed for controlling the shape and positioning of etched structures. One method of convex corner compensation that may be applied to aspects of the present invention is illustrated in FIGS. 27 and 28.

Figure 27:
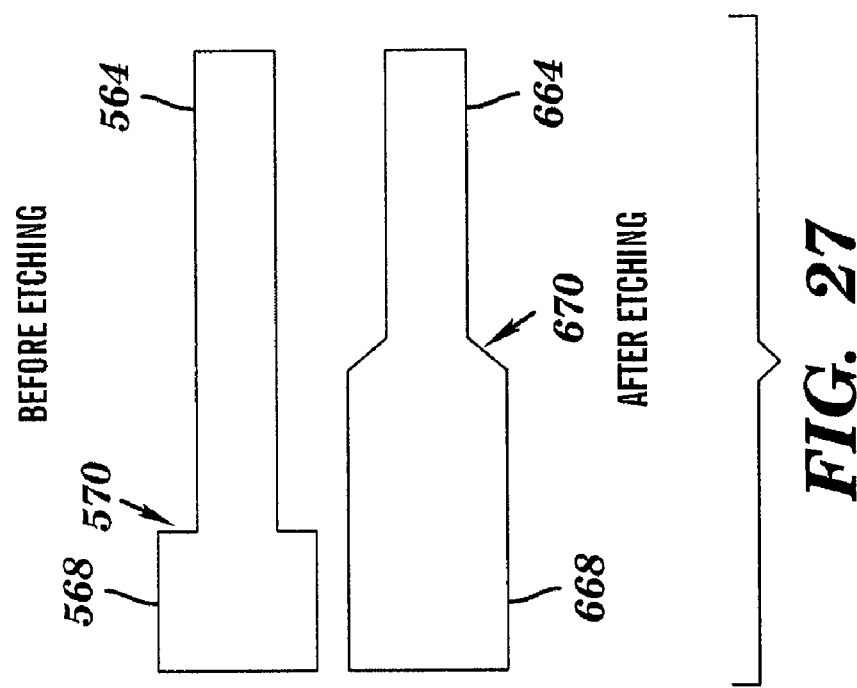
FIG. 27 is a schematic illustration of the typical size and shape of an etched structure when etching is practiced without convex corner compensation.

FIG. 27 is a schematic illustration of the typical size and shape of a mask for an etched structure, for example, a V-groove as discussed above, when etching is practiced without convex corner compensation and the typical resulting structure. FIG. 28 is a schematic illustration of the typical size and shape of a mask for an etched structure, for example, a V-groove, when etching is practiced with convex corner compensation. According to aspects of the invention, the top image in FIG. 27 represents a top plan view of a channel 564, for example, similar to channel 64, 164, or 464 described above, having a recess 568, for example, similar to recess 68, 168, or 468 described above. For instance, the top image in FIG. 27 may represent the appearance of the desired structures after etching or the image of the substrate as masked. According to aspects of the invention, the size and location of the transition between channel 564 and recess 568, indicated by arrow 570 in the top image of FIG. 27, is typically significant, if not critical, to the formation of the desired sensor according to aspects of the invention. However, without convex corner compensation, due to, for example, convex corner undercutting, the conjunction between larger and smaller structures, for instance, grooves, will be etched towards the smaller one. For example, the resulting structures created by etching, for example, with potassium hydroxide (KOH), are illustrated in the lower image of FIG. 27. The lower image of FIG. 27 represents the top plan view a channel 664, recess 668, and transition 670 produced by etching without convex corner compensation. Clearly, a comparison of the two images in FIG. 27 reveals that the shape and location of transition 670 has varied markedly from the desired shape and location of the desired transition 570.

Figure 28:
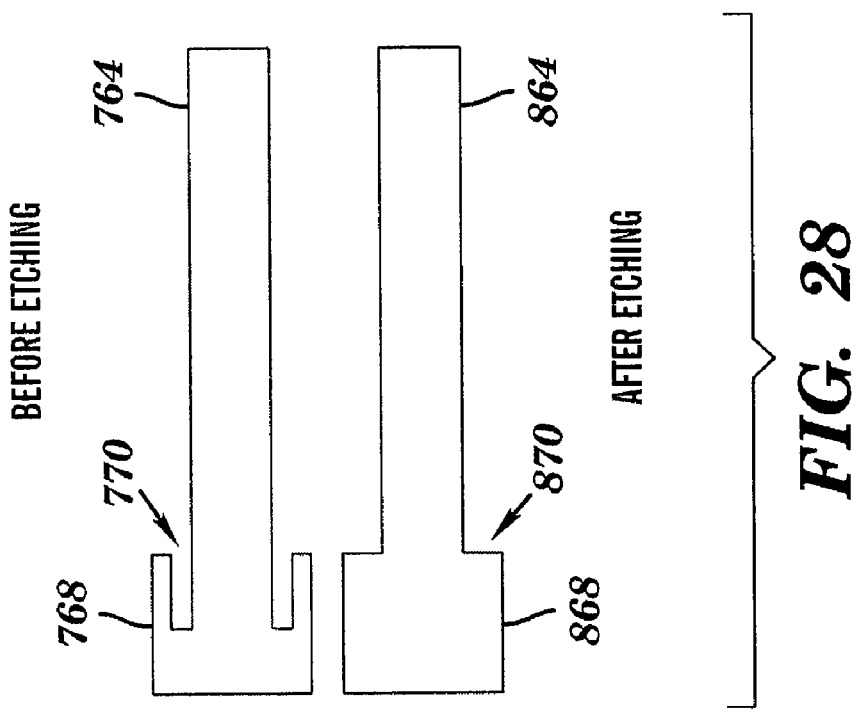
FIG. 28 is a schematic illustration of the typical size and shape of a structure when etching is practiced with convex corner compensation according to aspects of the invention.

In contrast to the images shown in FIG. 27, the images shown in FIG. 28 illustrate the desired shape of a mask for an etched structure and the resulting structure obtained by aspects of the invention. According to aspects of the invention, the top image in FIG. 28 represents a top plan view of a channel 764, for example, similar to channel 64, 164, or 464 described above, having a recess 768, for example, similar to recess 68, 168, or 468 described above. According to aspects of the invention, in order to more precisely provide the desired size and location of the transition between channel 764 and recess 768, indicated by arrow 870 in the bottom image of FIG. 28, at least one salient compensation structure is provided to reduce or even eliminate the movement of the structure or feature towards the smaller structure. For example, as shown in the upper image of FIG. 28, at least one protection bar 770 may be provided to minimize or prevent movement of the transition, for example, due to convex corner undercutting, for example, as disclosed by as Chu and Fang. The lower image of FIG. 28 represents the top plan view a channel 864, recess 868, and transition 870 produced by etching, for example, with potassium hydroxide (KOH), with convex corner compensation, that is, with protection bars 770. Clearly, a comparison of the two images in FIG. 28 reveals that the shape and location of transition 870 is much more consistent with the desired shape and location of the transition.

In another aspect of the invention, the accuracy of the position and dimensions of etched features may be improved. As is known in the art, the accuracy and quality of position and dimensions of a channel, groove, or recess in a substrate after etching, for example, wet anisotropic etching, is sensitive to the alignment accuracy between the etching window edge and the orientation of the crystal planes of the substrate, for example, of the single crystal silicon. Typically, the commercial standard for etching window edge alignment accuracy with the crystal planes of the substrate comprises an off-orientation accuracy of +/−1 degree. Aspects of the present invention can improve this off-orientation accuracy compared to prior art methods.

Figure 30:
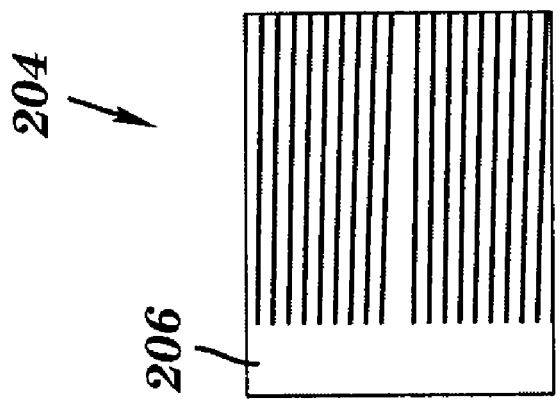
FIG. 30 is a schematic illustration or an etched pattern on a substrate according to an aspect of the invention.
Figure 29:
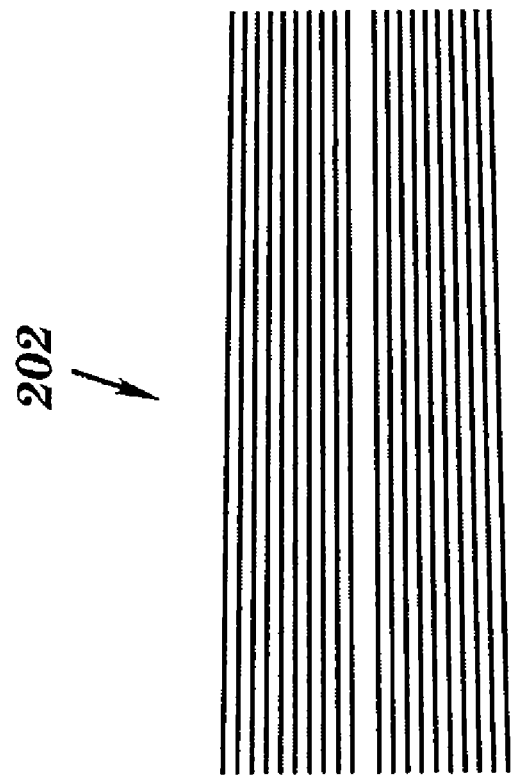
FIG. 29 is a schematic illustration of an etched pattern produced by a process to indicate the correct orientation of the crystal planes of a substrate according to an aspect of the invention.

FIGS. 29 and 30 illustrate one aspect of the invention that provides "orientation assistance" to the patterning of etched features. Aspects of the invention can provide etching window edge alignment accuracy with the crystal planes of the substrate with an off-orientation accuracy of greater than the industry standard +/−1.0 degrees. FIG. 29 is a schematic illustration of an etched pattern 202 produced by a process of etching a substrate in a first step to indicate the correct orientation of the crystal planes of the substrate, for example, by anisotropic wet etching of single crystal silicon. FIG. 30 is a schematic illustration or an etched pattern 204 on the substrate 206, for example, a silicon wafer, after etching, for example with potassium hydroxide (KOH). The lines in pattern 204 with non-correct orientation with respect to the substrate crystal planes will be etched away while the lines with correct orientation, that is, consistent with the substrate crystal planes, will survive the etching process and can then be used for reference in subsequent etching window placement and alignment. For example, if not aligned properly, the surfaces of the resulting channel or groove may not be smooth, but have undesirable steps, for example, like a staircase. By applying aspects of the invention, the dimensions and positions of etched features can be improved and smoother feature surfaces can be provided. For example, aspects of the invention can provide a dimensional and positional accuracy of +/−1.0 degree or finer, for instance, as fine a tolerance as +/−0.1 degrees has been realized by employing aspects of the invention.

Experimental Validation—Static Test

Figure 31:
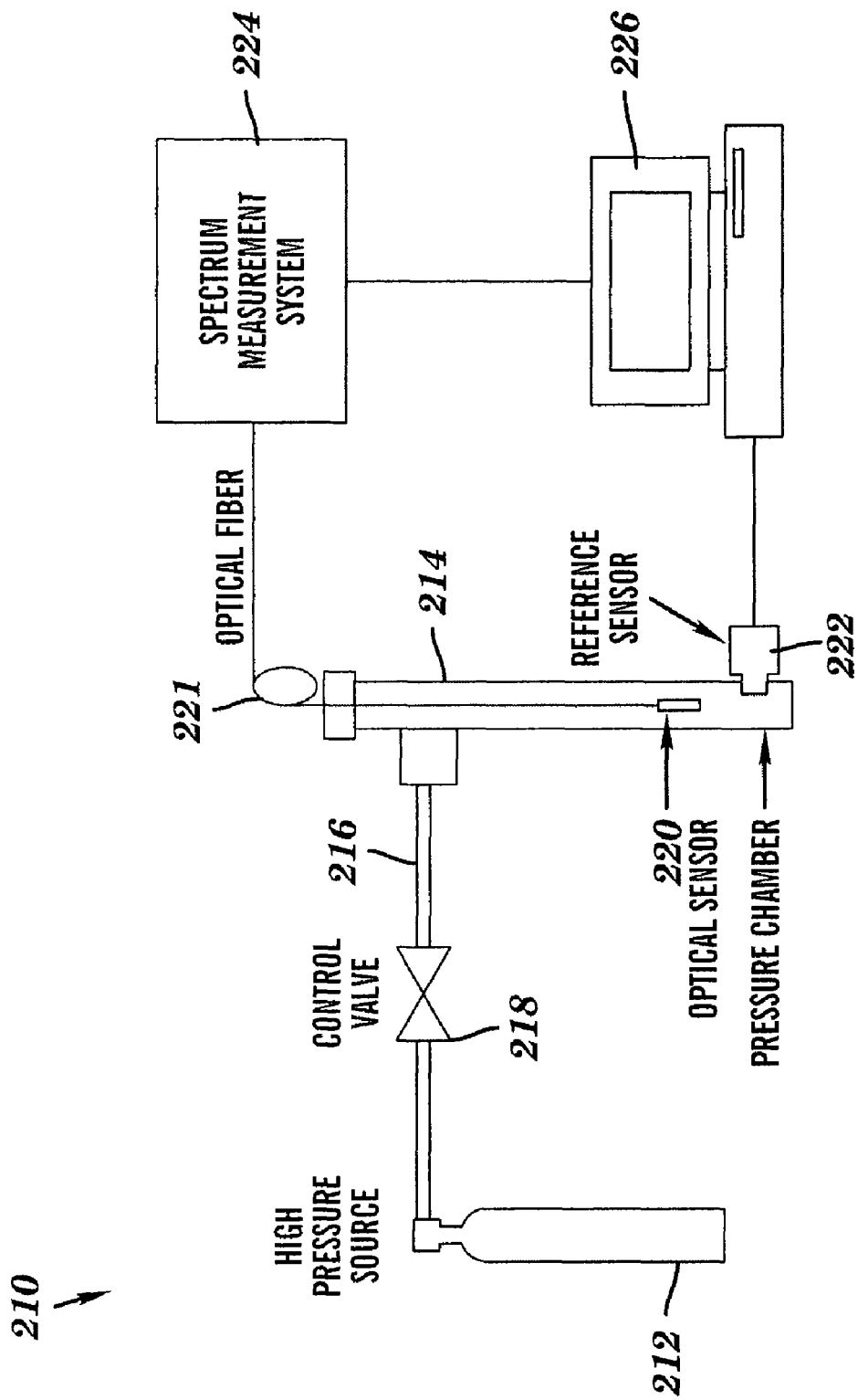
FIG. 31 is a schematic diagram of an experimental setup used to validate aspects of the invention.

Aspects of the invention were validated in laboratory trials. FIG. 31 is a schematic diagram of an experimental setup 210 used by the inventors to validate aspects of the invention. Setup 210 includes a pressurized gas source 212, such as an air tank, that is used to provide a high-pressure air to pressurize a pressure chamber 214. The flow of air is directed through a conduit 216 and is regulated by a control valve 218. A sensor 220 according to aspects of the invention having optical fiber 221 was tested side by side with a commercially available pressure transducer 222, specifically, an Omega model PX303 pressure transducer. The output of the reference pressure sensor 222 was assumed to be the true pressure value applied to the testing chamber 214 to evaluate the performance of the optical sensor 220. The outputs of sensor 220 and 222 were forwarded to a data acquisition and recording system including a spectrum measurement system 224 and a computer 226. The results of static testing are displayed in FIG. 32.

Figure 32:
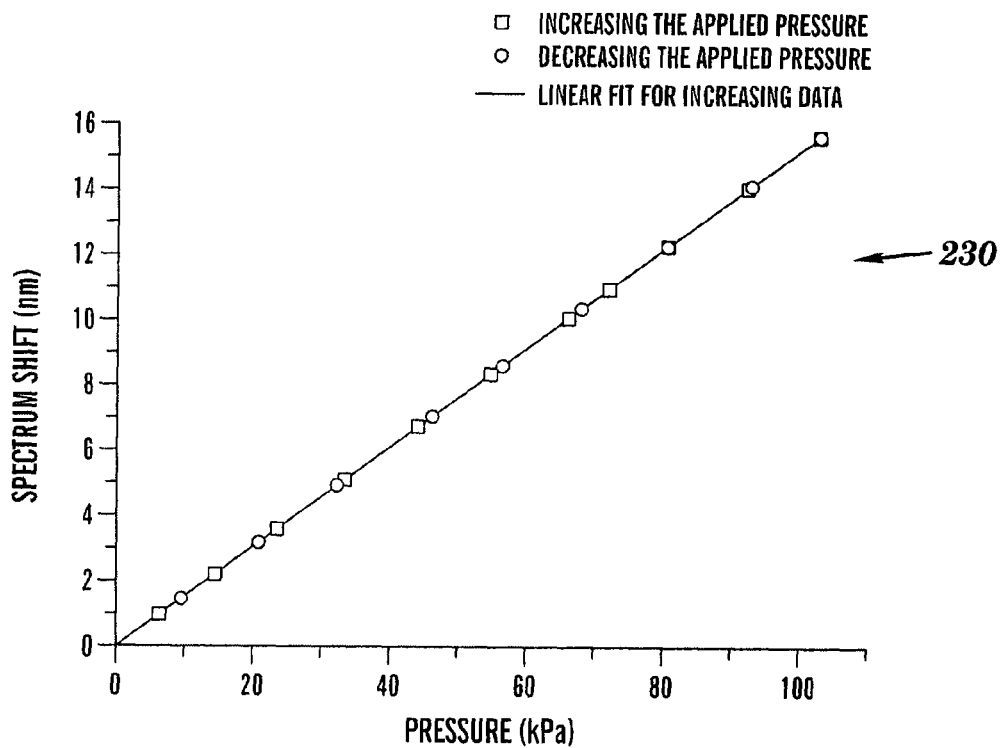
FIG. 32 is a graphical representation of the spectrum shifts collected with the setup shown in FIG. 31.

FIG. 32 is a graphical representation 230 of the spectrum shifts of the sensor 220 for data collected with the setup 210 of FIG. 31. Solid black squares in FIG. 22 represent the measured values of sensor 220 when pressure was increased consistently and the red (open black) squares are the measured values for sensor 220 when pressure was decreased consistently. FIG. 32 displays the comparative test of sensitivity, linearity, and hysteresis for the invention 220. The graph 230 indicates a sensitivity of spectrum shift of sensor 220 according to the invention is about 0.15 nanometers/kiloPascal (nm/kPa). The linearity of sensor 220 measurements is good with a correlation coefficient (R) of 0.99987. The maximum shift difference for bidirectional running at the same pressure is about 0.05 nm, which means a maximum hysteresis is about 0.32%. The sensitivity of the diaphragm deformation of the invention is about 4.64 nm/kPa, which is similar with the calculation results of 4.404 nm/kPa. Clearly, aspects of the present invention agree very well with a commercially available sensor.

Experimental Validation—Dynamic Test with Pressure Release

Figure 33:
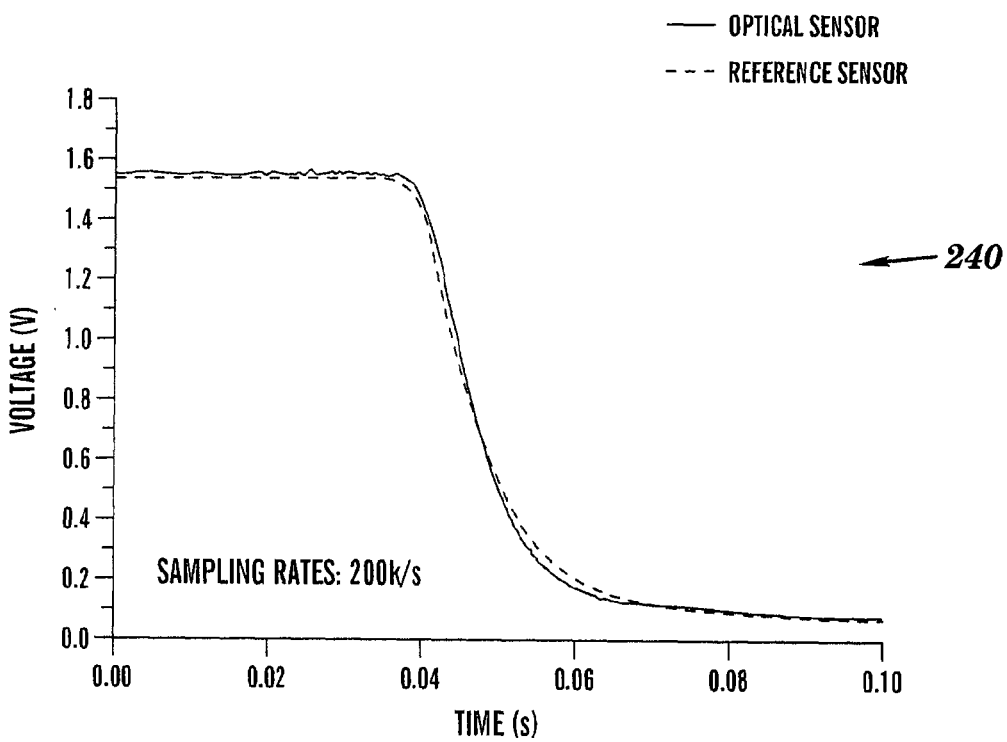
FIG. 33 is a graphical representation of the dynamic response of aspects of the invention as detected using the setup shown in FIG. 31.

FIG. 33 is a graphical representation 240 of the comparison of the dynamic response of sensor 220 compared to reference sensor 222 using the setup 210 shown in FIG. 31, but with a modified data acquisition system. The data acquisition system of system 210 was modified to measure the pressure change when the gas was released suddenly. In particular, a laser with fixed wavelength and a photo detector were used instead of the spectrum measurement system 224. The data was sampled at 200 kHz. FIG. 33 displays the voltage output by reference sensor 222 and optical sensor 220 according to the invention when the pressure is released quickly. As shown in FIG. 33, the reference sensor 222 (shown as a dashed line) responds to a fast pressure change from 90% to 50% within 7 milliseconds (ms) approximately. The optical sensor 220 (shown as a solid line) according to the invention, exhibits a similar response compared to reference sensor 222. However, based upon calculations, the bandwidth of the optical sensor 220 according to the invention has a dynamic performance that is much higher than the reference sensor 222. Quantifying the high-end dynamic range of optical sensor 220 is limited by the physical test setup 210 (for example, the speed of the pressure release) and the dynamic range of the reference sensor 222. High frequency performance testing of aspects of the invention are also underway.

Experimental Validation—A Balloon Explosion

Figure 34:
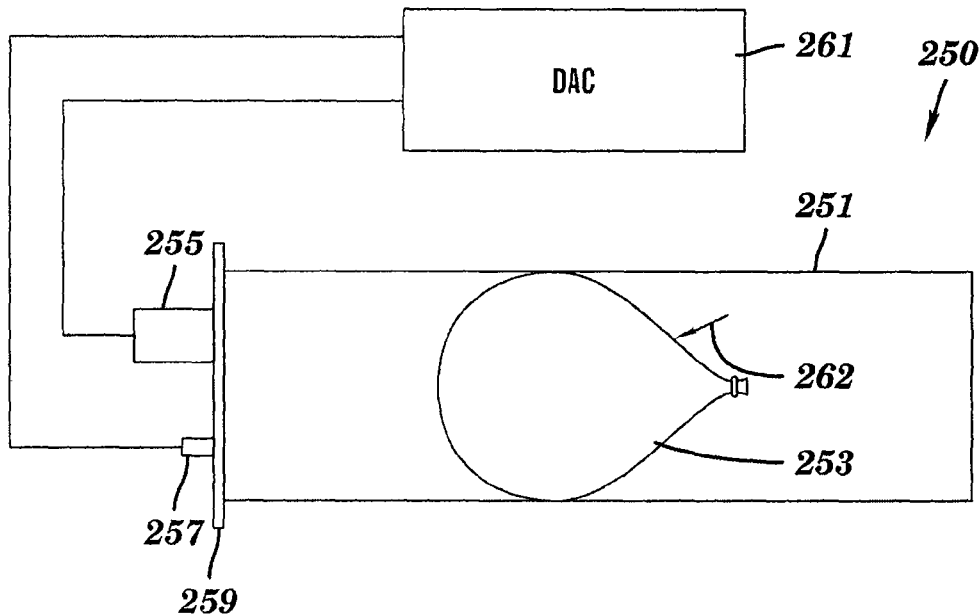
FIG. 34 is a schematic diagram of another testing system used to evaluate aspects of the invention.

An investigation of the comparative response of a sensor according to the present invention and a reference sensor for a blast event was also undertaken using a punctured balloon as a blast source. FIG. 34 provides a schematic diagram of the testing system 250 used in this investigation. A 4" polyvinyl chloride (PVC) tube 251 was used to confine the acoustic wave generated by a balloon 253. An electrical reference sensor 255 and the optical acoustic sensor 257 according to an aspect of the invention were mounted together on a Poly (methyl methacrylate) (PMMA) sheet 259 at the end of the PVC tube 251. The outputs of reference sensor 255 and optical sensor 257 were connected to a data acquisition system (DAC) 261.

Figure 35:
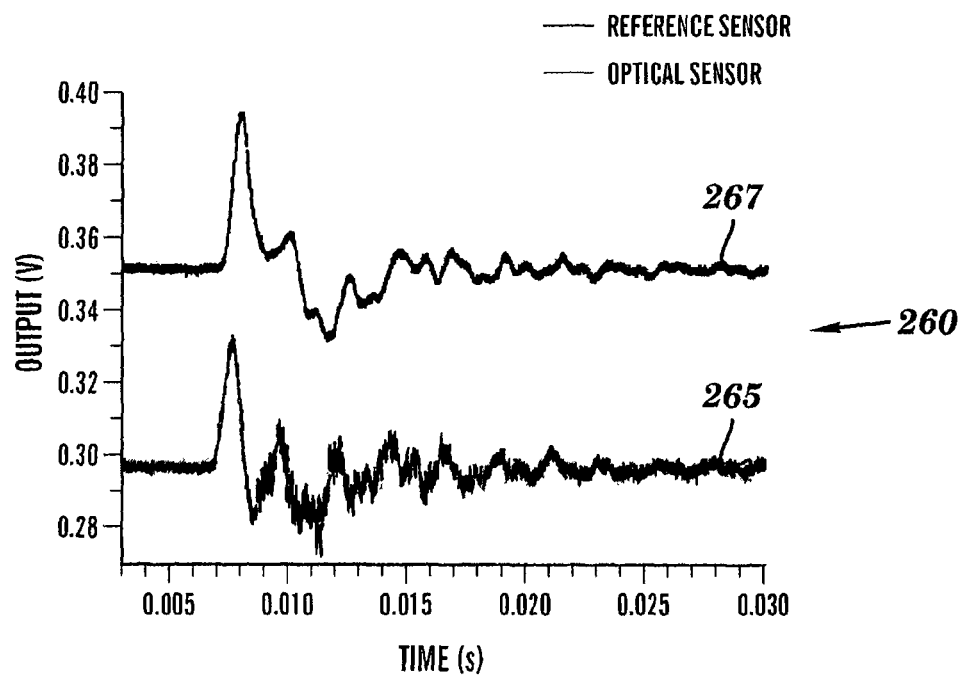
FIG. 35 is a graphical representation of the voltage output of aspects of the invention using the testing system shown in FIG. 34.

The balloon 253 was placed into the center of the PVC tube 251 and then punctured 262. The pressure wave generated by the popped balloon propagated to sensors 255 and 257 mounted at the end of tube 251. The sampling rate of the DAC system 261 was set to 500 kHz. FIG. 35 illustrates the results of the balloon testing for both sensors.

FIG. 35 is a graphical representation 260 of the voltage output by reference sensor 255 and optical sensor 257 to the balloon blast simulation illustrated in FIG. 34. In order to facilitate comparison of the output data, in graph 260, the signal 265 of reference sensor 255 was shifted −0.15 Volts (V) in comparison to the signal 267 of sensor 257 according to the invention. As seen in viewing FIG. 35, the responses from the two sensors are similar, though the output signal 265 of reference sensor 255 is somewhat smoother. The difference in quality of the signals may be due to a broad range of factors, including the lower response time of reference sensor 255 (that is, about 1 ms), the faster response time optical sensor 257, and the different mounting locations of the sensors, among other sources, which are being investigated.

Experimental Validation—Accuracy of Cavity Length

The inventors also investigated the quality or uniformity of the F-P cavity length that can be achieved according to aspects of the invention. For example, the accuracy of the length of "Cavity 1" shown in FIG. 5. In the testing summarized in FIG. 36, three nominal F-P cavity lengths were used: 15.643 μm, 23.368 μm, and 31.093 μm.

Figure 36:
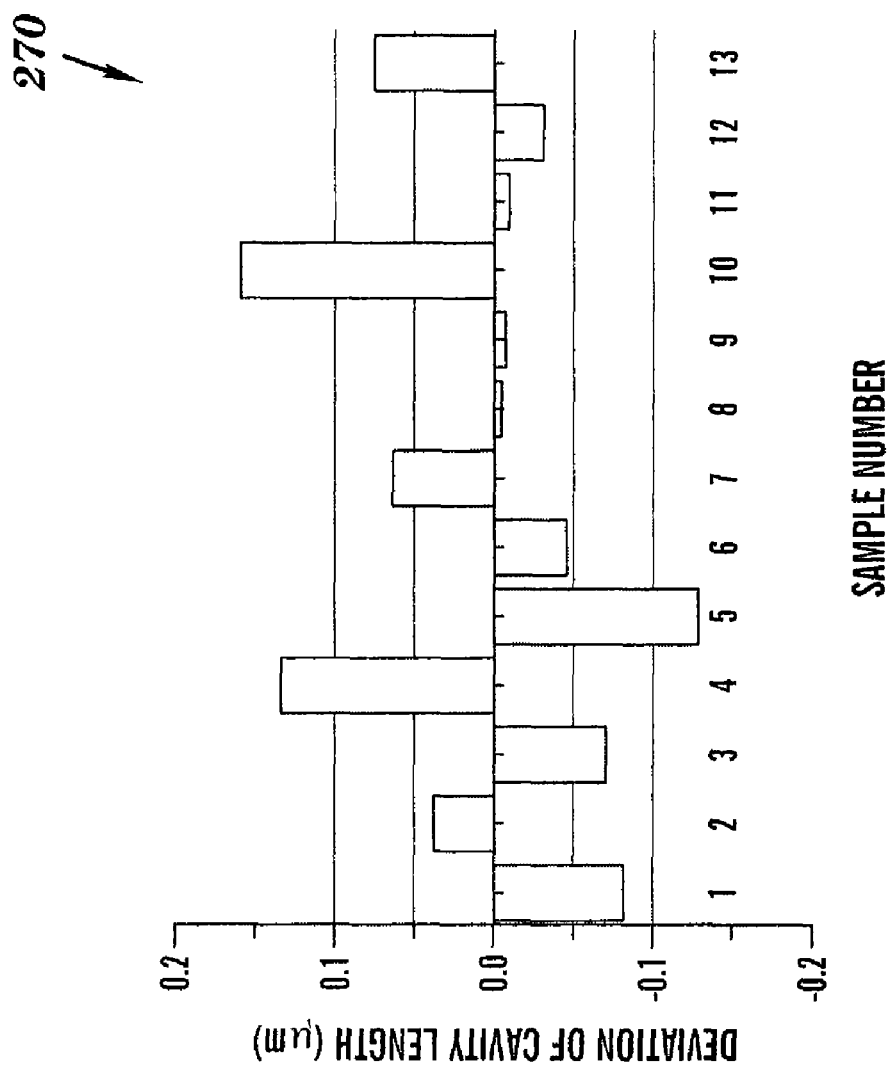
FIG. 36 is a graph of the deviation from a nominal dimension of a Fabry-Perot (F-P) cavity length according to aspects of the invention.

Thirteen v-groove type channels were fabricated on the same silicon wafer and then measured. The deviations of the cavity length from a nominal design value are shown the in FIG. 36. FIG. 36 is a bar graph 270 of the deviation from nominal dimension of an F-P cavity length according to aspects of the invention. As shown in FIG. 36, six (6) out of the 13 samples are in the +/−0.05 μm range of nominal length (which, as discussed above, corresponds to a 1/16 period shift of the spectrum). As also shown in FIG. 36, ten (10) out of the 13 samples are within the +/−0.1 μm range of nominal length. The inventors believe that since imperfectness or deviations from the desired nominal cavity length may mainly come from defects in the substrate, for example, a silicon crystal, the precision of the cavity length of aspects of the invention may be improved by using high quality silicon wafers for substrates, for example, silicon wafers fabricated especially for Microelectromechanical System (MEMS) application and using high purity etchant.

Figure 37:
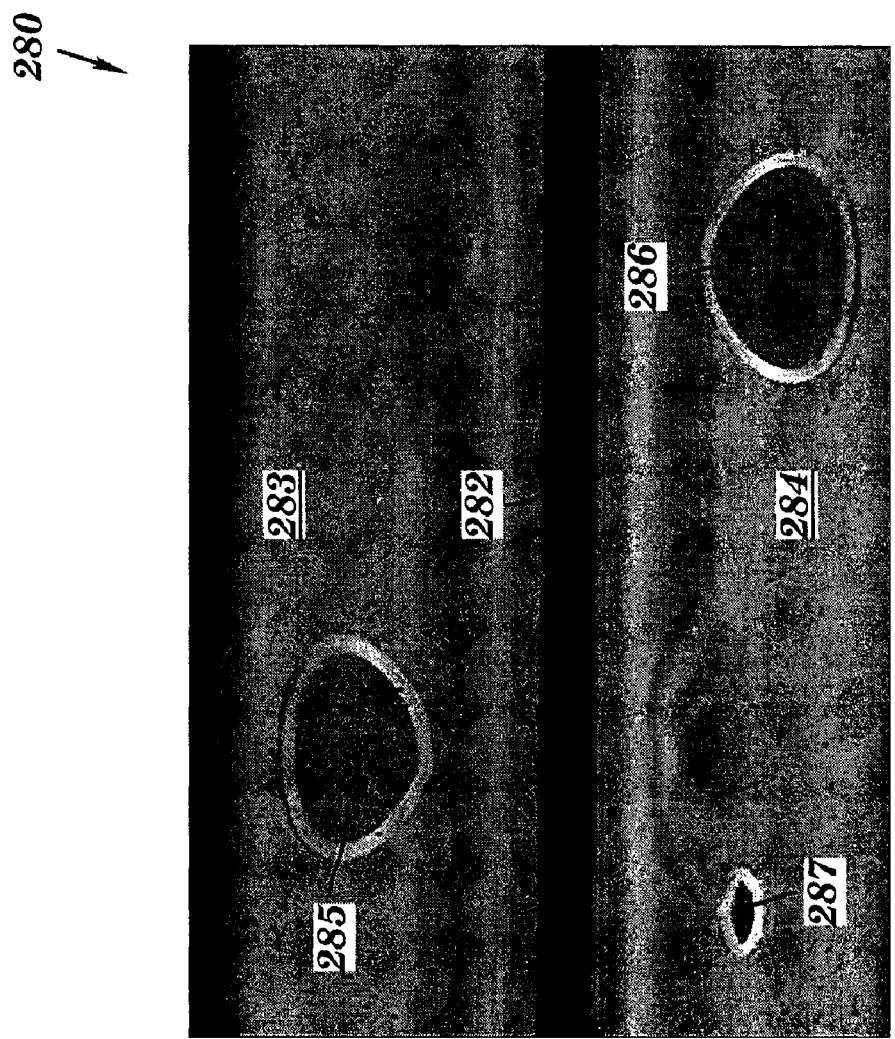
FIG. 37 is a top plan microscope photo of a v-groove-type channel having circular diaphragms according to aspects of the invention.

FIG. 37 is a top plan microscope photo 280 of a v-groove-type channel having circular diaphragms according to aspects of the invention. The dark horizontal band 282 in photo 280 is the flat bottom surface of the V-groove, for example, as shown in FIG. 3B, having sloping sidewalls 283, 284 and circular diaphragms (which appear elliptical in this view). In photograph 280 in FIG. 39, the top side wall 283 includes one diaphragm 285 and the bottom side wall 284 includes one larger diaphragm 286 and one smaller diaphragm 287. In the actual diaphragms shown, the silicon oxide in the substrate beneath the diaphragms was removed by 49% solution of HF.

As shown in FIG. 37, the dark central circles shown for diaphragms 285, 286, and 287 are the through holes of the cavity (cavity 378 in FIGS. 24-26) and the bright circular bands about the central circles are the areas about the through holes (378) where the silicon oxide (371 in FIGS. 24-26) between the silicon nitride (372 in FIGS. 24-26) and silicon substrate (356 in FIGS. 24-26) has been removed by the HF etching (see FIGS. 24-26 and the associated discussion). As indicated by FIG. 37, the high-concentration hydrofluoric acid (HF) can reach the silicon oxide (371) via the small deep holes (378) etched from the back side of silicon wafer (356) according to aspects of the invention to provide the desired diaphragm release.

Though aspects of the present invention were developed for use in fabricating AE sensors, it is recognized that aspects of the invention are not limited to AE sensor fabrication, but can also be applied in the fabrication of other diaphragm-type sensors, especially, in diaphragm-based optical fiber sensor. Examples include pressure sensors, accelerometers, and temperature sensors. It is also recognized that aspects of the invention are also applicable to non-sensor technologies, for example, to the fabrication of any type of diaphragm or membrane that may be desired in the MEMS fabrication art.

It will be clear from the above description to those of skill in the art that aspects of the present invention include the fabrication of silicon-based anisotropic wet etched V-grooves as a diaphragm base structure; the use of photolithographic methods to achieve precise F-P cavity length control and high yield; the use of angled and polished wave guides to deliver and collect light to and from the diaphragm; and the fabrication of very thin and high quality diaphragms. Among other advantages, aspects of the present invention provide many advantages over the prior art methods and sensors. Specifically, among other things, aspects of the present invention provide:

a simple fabrication process employing substantially standardized MEMS processing techniques;

precise cavity length control based on a novel technology that can precisely control F-P cavity length to better than +/−0.05 micros;

precise diaphragm thickness control;

ultra-high sensitivity sensors having diaphragm thicknesses that can be fabricated to tens of nanometers;

wide ranging applications, including high pressure measurement, for example, using thick diaphragms of tens of microns in thickness;

a flexible design that can be adapted to specific applications, including a metal layer can be easily added by thermal evaporation or sputtering method;

simplified assembly using, for example, V-groove channels and optical fiber can be easily assembled and aligned to the substrate;

a robust structure that provides hard contact between the wave guide and substrate;

good temperate stability due to the small cavity length;

good leak-proof quality since sensors according to the invention can be sealed using standard MEMS bonding technology; and a high yield and low cost manufacturing process where different sizes of diaphragms can be fabricated on a single substrate at the same time and selected for assembly on different sensors having varying specifications.

While several aspects of the present invention have been described and depicted herein, alternative aspects may be apparent to those skilled in the art to accomplish the same objectives. Accordingly, it is intended by the appended claims to cover all such alternative aspects as fall within the true spirit and scope of the invention.

The invention claimed is:

1. A method for fabricating a sensor, the method comprising:
providing an elongated open channel in a top surface of a substrate, the open channel providing a first surface and a direction of elongation;
wherein providing an elongated open channel in the surface of the substrate comprises providing an elongated v-groove in the surface of the substrate;
wherein the first surface comprises a side surface of the v-groove;
removing at least some material from at least a portion of the first surface of the open channel to provide a second surface in the open channel displaced from the first surface and parallel to the first surface;
positioning a diaphragm on the second surface, the diaphragm having a top surface and a bottom surface, the diaphragm being adapted to deflect in response to a stimulus;
removing at least some material from the substrate beneath the diaphragm; and
positioning an elongated wave-guide having a beveled end in the elongated open channel wherein an outer surface of the wave-guide contacts the first surface and wherein the beveled end is positioned over the diaphragm to define an interferometric cavity between the diaphragm and the outer surface of the wave-guide.

2. The method as recited in claim 1, wherein the first surface of the open channel comprises a first depth from the top surface of the substrate and wherein the second surface comprises a second depth from the top surface of the substrate, greater than the first depth.

3. The method as recited in claim 1, wherein providing the elongated open channel in the top surface of the substrate comprises etching the top surface of the substrate.

4. The method as recited in claim 1, wherein positioning the diaphragm on the second surface comprises depositing a material on the second surface.

5. The method as recited in claim 1, wherein removing at least some material from the substrate to expose at least some of the bottom surface of the diaphragm comprises etching a hole in the substrate to expose at least some of the bottom surface of the diaphragm.

6. The method as recited in claim 1, wherein positioning the elongated wave-guide comprises positioning an optical fiber having the beveled end in the elongated open channel.

7. The method as recited in claim 1, wherein the stimulus comprises one of an acoustic wave and an acoustic emission wave.

8. The method as recited in claim 1, wherein the sensor is adapted to detect one or more of elastic strain waves, compression waves, longitudinal waves, dynamic pressure waves, static pressure, temperature, and acceleration.

9. The method as recited in claim 1, wherein the method comprises a method for fabricating a plurality of sensors; and the method further comprises characterizing each of the plurality of sensors.

10. The method as recited in claim 9, wherein the method comprises a method for fabricating a plurality of sensors on a single substrate.

11. A sensor comprising:
an elongated open channel in a top surface of a substrate, the open channel providing a first surface;
wherein the elongated open channel in the surface of the substrate comprises an elongated v-groove in the surface of the substrate;
wherein the first surface comprises a side surface of the v-groove;
a recess in at least a portion of the first surface of the open channel providing a second surface displaced from the first surface, the second surface being parallel to the first surface;
a diaphragm positioned on the second surface, the diaphragm having a top surface and a bottom surface;
a cavity in the second surface beneath the diaphragm exposing at least a portion of the bottom surface of the diaphragm; and
an elongated wave-guide adapted to transmit electromagnetic radiation, the wave-guide having a beveled end positioned in the elongated open channel wherein an outer surface of the wave-guide contacts the first surface and wherein the beveled end is positioned over the diaphragm to transmit radiation to and receive radiation from the diaphragm and to define an interferometric cavity length between the diaphragm and an outer surface of the wave-guide.

12. The sensor as recited in claim 11, wherein the first surface of the open channel comprises a first depth from the top surface of the substrate and wherein the second surface comprises a second depth from the top surface of the substrate, greater than the first depth.

13. The sensor as recited in claim 11, wherein the diaphragm comprises a material positioned on the second surface.

14. The sensor as recited in claim 11, wherein the cavity comprises a hole in the substrate positioned to expose at least some of the bottom surface of the diaphragm.

15. A method for sensing a stimulus comprising:
providing an elongated open channel in a top surface of a substrate, the open channel providing a first surface;
wherein the elongated open channel in the surface of the substrate comprises an elongated v-groove in the surface of the substrate;
wherein the first surface comprises a side surface of the v-groove;
providing a recess in at least a portion of the first surface to provide a second surface displaced from the first surface, the second surface being parallel to the first surface;
positioning a diaphragm on the second surface of the recess, the diaphragm adapted to deflect in response to the stimulus;
providing a cavity in the substrate beneath the diaphragm;
positioning an elongated wave-guide having a beveled end in the elongated open channel wherein an outer surface of the wave-guide contacts the first surface and wherein the beveled end is positioned over the diaphragm to define an interferometric cavity length between the diaphragm and an outer surface of the wave-guide;
transmitting a first electromagnetic signal from the beveled end upon the diaphragm;
receiving a second electromagnetic signal reflected from the diaphragm; and
comparing the second electromagnetic signal to a first signal to detect deflection of at least a portion of the diaphragm to characterize the stimulus deflecting the diaphragm.

16. The method as recited in claim 15, wherein the first surface of the open channel comprises a first depth from the top surface of the substrate and wherein the second surface comprises a second depth from the top surface of the substrate, greater than the first depth.

17. The method as recited in claim 15, wherein providing the cavity in the substrate comprises etching the cavity in the second surface.

18. The method as recited in claim 15, wherein positioning a diaphragm on the second surface comprises depositing a material on the second surface to form the diaphragm.

19. The method as recited in claim 15, wherein positioning an elongated wave-guide having the beveled end in the elongated open channel comprises positioning an optical fiber having the beveled end in the elongated open channel.

20. The method as recited in claim 15, wherein transmitting the first electromagnetic signal from the beveled end comprises transmitting the first electromagnetic signal along the wave-guide and reflecting the first electromagnetic signal from the beveled end and upon the diaphragm.

21. The method as recited in 15, wherein receiving the second electromagnetic signal comprises receiving the second electromagnetic signal and reflecting the second electromagnetic from the beveled end and transmitting the second electromagnetic signal along the wave-guide.

22. The method as recited in claim 15, wherein comparing the first electromagnetic signal to the second electromagnetic signal to characterize deflection of at least the portion of the diaphragm comprises transmitting the second electrical signal to an interferometer signal analyzer.

23. The method as recited in claim 15, wherein the method further comprises transmitting a source electromagnetic signal along the elongated wave-guide and reflecting the source electromagnetic signal from the beveled end toward the diaphragm; reflecting at least some of the source electromagnetic signal from a sidewall of the waveguide to provide the reference electromagnetic signal; and transmitting at least some of the source electromagnetic signal through the sidewall to provide the first electromagnetic signal.

24. The method as recited in claim 15, wherein the method is adapted to sense one or more of elastic strain waves, compression waves, longitudinal waves, dynamic pressure waves, static pressure, acceleration, and temperature.

25. The method as recited in claim 15, wherein the method is adapted to sense acoustic emission waves.

26. The method as recited in claim 15, wherein the interferometric cavity length is controlled to a tolerance of +/−0.05 micrometers or less.

27. The method as recited in claim 15, wherein the diaphragm comprises a diaphragm having a thickness less than 0.05 micrometers, and wherein the interferometric cavity length comprises a length having a tolerance of +/−0.05 micrometers or less.

28. The method as recited in claim 15, wherein transmitting a first electromagnetic signal from the beveled end upon the diaphragm and receiving a second electromagnetic signal reflected from the diaphragm, comprises transmitting a first electromagnetic signal from the beveled end upon the top surface of the diaphragm; and wherein receiving a second electromagnetic signal reflected from the diaphragm comprises receiving the second electromagnetic signal reflected from the top surface of the diaphragm.

29. The method as recited in claim 15, wherein providing a cavity in the second surface includes providing an aperture having a distal end positioned to receive a stimulus and transmit the stimulus through the aperture.

30. The method as recited in claim 29, wherein a distal end of the aperture comprises an open distal end.

31. The method as recited in claim 29, wherein a distal end of the aperture comprises a closed distal end.

32. The method as recited in claim 31, wherein the cavity comprises a sealed cavity.

* * * * *